US012036035B2

(12) United States Patent
Gough et al.

(10) Patent No.: US 12,036,035 B2
(45) Date of Patent: Jul. 16, 2024

(54) SYSTEMS, DEVICES AND METHODS FOR ESTIMATING BLOOD GLUCOSE CONCENTRATIONS FROM SIGNALS OF SENSORS DEPLOYED IN TISSUE

(71) Applicant: The Regents of the University of California, Oakland, CA (US)

(72) Inventors: David A. Gough, Solana Beach, CA (US); Shaghayegh Abbasi, San Diego, CA (US); Stefanie Heinz, Kissing (DE)

(73) Assignee: The Regents of the University of California, Oakland, CA (US)

( * ) Notice: Subject to any disclaimer, the term of this patent is extended or adjusted under 35 U.S.C. 154(b) by 973 days.

(21) Appl. No.: 16/962,832

(22) PCT Filed: Jan. 16, 2019

(86) PCT No.: PCT/US2019/013876
§ 371 (c)(1),
(2) Date: Jul. 16, 2020

(87) PCT Pub. No.: WO2019/143741
PCT Pub. Date: Jul. 25, 2019

(65) Prior Publication Data
US 2021/0059602 A1    Mar. 4, 2021

(51) Int. Cl.
*A61M 5/172*       (2006.01)
*A61B 5/00*        (2006.01)
(Continued)

(52) U.S. Cl.
CPC ........ *A61B 5/4839* (2013.01); *A61B 5/14532* (2013.01); *A61B 5/14865* (2013.01);
(Continued)

(58) Field of Classification Search
CPC . A61B 5/1455; A61B 5/14532; A61B 5/1495; A61B 5/4839; A61B 5/7275;
(Continued)

(56) References Cited

U.S. PATENT DOCUMENTS

| 4,671,288 A | 6/1987 | Gough |
| 7,248,912 B2 | 7/2007 | Gough et al. |

(Continued)

FOREIGN PATENT DOCUMENTS

| WO | 2010114929 A1 | 10/2010 | |
| WO | WO-2010114929 A1 * | 10/2010 | ......... A61B 5/14532 |

OTHER PUBLICATIONS

Kovatchev et al. "Comparison of the Numerical and Clinical Accuracy of Four Continuous Glucose Monitors" Diabetes Care, Jun. 2008: 31(6): pp. 1160-1164 ("Kovatchev"). (Year: 2008).*
(Continued)

*Primary Examiner* — Deanna K Hall
(74) *Attorney, Agent, or Firm* — Perkins Coie LLP

(57) ABSTRACT

Disclosed are systems, devices and methods for estimating blood glucose parameters, including blood glucose concentration glucose sensor signals. In some aspects, a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; isolating error associated with the matched blood glucose reference values to determine a residual error time series, wherein the isolated error includes a composite error comprising a measurement error, a process error, and random error; and producing
(Continued)

estimated blood glucose values for true blood glucose of the subject by adding the reference blood glucose concentration values to the residual error time series.

23 Claims, 13 Drawing Sheets

(51) Int. Cl.

| | | |
|---|---|---|
| A61B 5/145 | (2006.01) | |
| A61B 5/1486 | (2006.01) | |
| A61M 5/142 | (2006.01) | |
| G06F 16/23 | (2019.01) | |
| G16H 10/40 | (2018.01) | |
| G16H 20/17 | (2018.01) | |
| G16H 40/40 | (2018.01) | |
| G16H 40/67 | (2018.01) | |
| G16H 50/20 | (2018.01) | |
| G16H 50/30 | (2018.01) | |
| G16H 50/70 | (2018.01) | |

(52) U.S. Cl.
CPC ............ *A61B 5/681* (2013.01); *A61B 5/7221* (2013.01); *A61B 5/7275* (2013.01); *A61M 5/14244* (2013.01); *A61M 5/1723* (2013.01); *G06F 16/2365* (2019.01); *G16H 10/40* (2018.01); *G16H 20/17* (2018.01); *G16H 40/40* (2018.01); *G16H 40/67* (2018.01); *G16H 50/20* (2018.01); *G16H 50/30* (2018.01); *G16H 50/70* (2018.01); *A61B 5/6833* (2013.01); *A61M 2205/3576* (2013.01); *A61M 2205/502* (2013.01); *A61M 2205/52* (2013.01); *A61M 2205/581* (2013.01); *A61M 2205/583* (2013.01); *A61M 2230/201* (2013.01)

(58) Field of Classification Search
CPC .............. A61B 5/7221; A61M 5/1723; A61M 2205/3523; A61M 2205/502; A61M 2205/52; A61M 2230/201; G16H 50/70
See application file for complete search history.

(56) References Cited

U.S. PATENT DOCUMENTS

| | | |
|---|---|---|
| 7,336,984 B2 | 2/2008 | Gough et al. |
| 2004/0024553 A1 | 2/2004 | Monfre et al. |
| 2011/0130970 A1* | 6/2011 | Goode, Jr. ........... A61B 5/0031 702/19 |
| 2017/0027526 A1 | 2/2017 | Maruo |

OTHER PUBLICATIONS

Bremer et al. "Perspectives in Diabetes: Is Blood Glucose Predictable From Previous Values?" Diabetes, Mar. 1999, 48, 445-451.
Facchinetti et al. "Real-Time Improvement of Continuous Glucose Monitoring Accuracy" Diabetes Care, 2013, vol. 36, pp. 793-800.
Gough et al. "Frequency Characterization of Blood Glucose Dynamics" Annals of Biomedical Engineering, 31, 2003, pp. 91-97.
Gough, et al. "Function of an Implanted Tissue Glucose Sensor for More than 1 Year in Animals" Science Translational Medicine, 2010, vol. 2, No. 4, 42ra53.
Heinz, S. "Blood glucose estimation from implanted sensor signal for diabetes" Bachelor Thesis, UC San Diego, Oct. 15, 2017. 32 pages.
ISA, International Search Report and Written Opinion for International Patent Application No. PCT/US2019/013876. Mail Date: Mar. 26, 2019. 15 pages.
Kovatchev et al. "Comparison of the Numerical and Clinical Accuracy of Four Continuous Glucose Monitors" Diabetes Care, Jun. 2008: 31(6): pp. 1160-1164.
Kumosa et al. "Permeability of subcutaneous tissues surrounding long-term implants to oxygen" Biomaterials, 2014, vol. 35, pp. 8287-8296.
Lucisano et al. "Glucose Monitoring in Individuals with Diabetes Using a Long-Term Implanted Sensor/Telemetry System and Model" IEEE Transactions on Biomedical Engineering, 64(9), Sep. 2017, 1982-1993.
Rahaghi, et al. "Blood Glucose Dynamics" Diabetes Technology & Therapeutics, 10(2), 2008, 81-94.
Simon "Optimal State Estimation" 2006, John Wiley & Sons, Inc. Hoboken, N.J. 550 pages.

* cited by examiner

SYSTEMS, DEVICES AND METHODS FOR ESTIMATING BLOOD GLUCOSE CONCENTRATIONS FROM SIGNALS OF SENSORS DEPLOYED IN TISSUE

CROSS-REFERENCE TO RELATED APPLICATIONS

This patent document is a 371 National Phase Application of International Application No. PCT/US2019/013876, filed on Jan. 16, 2019, which claims priorities to and benefits of U.S. Provisional Patent Application No. 62/618,013 entitled "SYSTEMS, DEVICES AND METHODS FOR ESTIMATING BLOOD GLUCOSE CONCENTRATIONS FROM SIGNALS OF SENSORS DEPLOYED IN TISSUE" filed on Jan. 16, 2018. The entire content of the aforementioned patent applications is incorporated by reference as part of the disclosure of this patent document.

TECHNICAL FIELD

This patent document relates to analyte sensor systems, devices and methods, in particular for glucose monitoring.

BACKGROUND

Diabetes mellitus, commonly referred to as diabetes, is a metabolic disease associated with inappropriate blood glucose concentrations due to insufficient production or use of insulin by the body. Diabetes is wide-spread condition, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. Gestational diabetes can occur during pregnancy when a pregnant woman develops a high blood glucose level, which can develop into type 2 diabetes, but often resolves after the pregnancy.

SUMMARY

Disclosed are systems, devices and methods for estimating blood glucose parameters, including blood glucose concentration, from signals of glucose sensors of various types, such as those that are fully implanted subcutaneously in tissues, inserted percutaneously (through the skin) in tissues, and/or deployed cutaneously (on the surface of skin or tissues), for individuals with diabetes and other medical conditions. The disclosed systems, devices and methods operate in an anti-causal mode, in which tissue sensor signals lead to serial estimates of blood glucose concentration.

Implementations of example embodiments of the disclosed methods, devices and systems in accordance with the present technology can include one or more of the following features. In some implementations, the disclosed systems, devices and methods include isolating individual sources of error contained in continuous and discrete glucose sensor signals, e.g., in which errors can include measurement error due to background variations of tissue oxygen and microvascular perfusion of tissues at the implant site; process error or diffusional lag error due to mass transport of glucose from the local tissue microvasculature to the sensor; random error present to some extent in almost all signals; and residual error remaining after effectively estimating and removing the measurement, process and random errors. The residual error represents the actual unresolved inaccuracy of the blood glucose estimate.

Also disclosed are systems, devices and methods for determining optimal dynamic parameters of the estimator, and for continuous, discrete-time, and/or real-time use of the estimator. Also disclosed are systems, devices and methods for using blood glucose estimates determined by the estimator to predict future blood glucose estimates ahead of present values. Also disclosed are systems, devices and methods for extending the sensor response to the full dynamic range of natural biological glucose excursions in individuals with diabetes. Also disclosed are systems, devices and methods for estimating temporal sampling errors in sensor operation. Also disclosed are systems, devices and methods for evaluating the accuracy of the estimated blood glucose compared to reference blood glucose, such as mean absolute relative difference, or MARD, and others.

Implementations of the disclosed systems, devices and methods can provide improved accuracy over signal interpretation methods based on correlation between blood glucose concentration and sensor signals, and other conventional methods. For example, various means of anti-diabetes therapy can be made possible based on the blood glucose estimates, e.g., such as administration of insulin and other medications, application of the artificial pancreas in various forms, management of diet, exercise, and body weight, and other means of disease management.

In some aspects, a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; isolating error associated with the matched blood glucose reference values to determine a residual error time series, wherein the isolated error includes a composite error comprising a measurement error, a process error, and random error; and producing estimated blood glucose values for true blood glucose of the subject by adding the reference blood glucose concentration values to the residual error time series.

In some aspects, a device for estimating blood glucose concentration from signals of glucose sensors includes a data processing device comprising a processor and a memory in communication with a glucose sensor, the data processing unit including an estimator module operable to: obtain a set of time-series values that includes tissue glucose sensor values from a glucose sensor and reference blood glucose concentration values associated with a subject, generate a set of matched blood glucose reference values by determining a temporal matching of the tissue glucose sensor values and the reference blood glucose concentration values, isolate error associated with the matched blood glucose reference values to determine a residual error time series, wherein the isolated error includes a composite error comprising a measurement error, a process error, and random error, and produce estimated blood glucose values for true blood glucose of the subject by adding the reference blood glucose concentration values to the residual error time series.

In some aspects, a system for estimating blood glucose concentration from signals of glucose sensors includes a glucose sensor acquire glucose measurements from a subject; and a data processing device comprising a processor and a memory in communication with the glucose sensor, the data processing unit including an estimator module operable to: obtain a set of time-series values that includes a tissue glucose sensor values from a glucose sensor and reference blood glucose concentration values associated with a subject, generate a set of matched blood glucose reference values by determining a temporal matching of the tissue glucose sensor values and the reference blood glucose concentration values, isolate error associated with the matched blood glucose reference values to determine a residual error time series, wherein the isolated error includes a composite error comprising a measurement error, a process error, and random error, and produce estimated blood glucose values for true blood glucose of the subject by adding the reference blood glucose concentration values to the residual error time series.

In some aspects, a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; determining a composite error in measured glucose by subtracting the reference blood glucose concentration values from the matched blood glucose reference values; determining a residual error of the set of time-series values by estimating and subtracting at least some of individual components of the determined composite error, wherein the components of the composite error include measurement error, process error, and random error; and producing estimated blood glucose values for true blood glucose of the subject by adding the reference blood glucose concentration values to the determined residual error.

In some aspects, a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; determining a composite error in measured glucose by subtracting the reference blood glucose concentration values from the matched blood glucose reference values; estimating individual error components in measured glucose including measurement error, process error, and random error; and producing estimated reference blood glucose values of the subject by subtracting the estimated error components from the matched blood glucose reference values.

The subject matter described in this patent document can be implemented in specific ways that provide one or more of the following features.

DETAILED DESCRIPTION

Figure 1A:
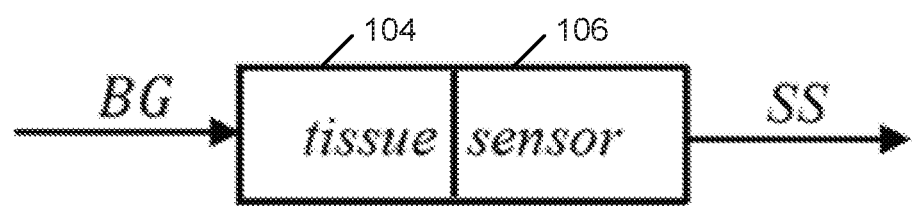
FIG. 1A shows a diagram depicting the conventional approach using the causal mode of producing a tissue glucose signal from blood glucose.

Diabetes is a major disease affecting people of all populations and age groups. All therapies for diabetes are intended to achieve close blood glucose control, and achieving such close control requires blood glucose monitoring. Close blood glucose control has been shown to reduce destructive "long-term complications" of diabetes, such as retinal damage, kidney failure, amputations, and cardiovascular damage, as well as debilitating and life-threatening short-term hypoglycemia. Attainment of close control requires (1) glucose concentration measurements, using some type of glucose sensor device; (2) a controller or control 'law' to direct the application of a corrective therapy, such as, for example, rules or protocols for insulin administration, based on measured blood glucose concentration; and (3) medication administration for correction of glucose imbalances, such as insulin administration, by a medicament injection device such as a syringe, an insulin injection device (such as an "insulin pen"), or automated or semi-automated insulin delivery device such as implanted or external insulin pumps activated by algorithmic-based controllers or "artificial pancreas." Furthermore, attainment of close blood glucose control and diabetes management can further benefit from glucose-dependent behavior modification, which includes attention and management of exercise, diet and body weight; warning and avoidance of hypoglycemia; controlled administration of glucagon and other medications; and other means. Accuracy of glucose sensing is crucial to the effectiveness of these therapies.

Glucose monitoring requires diabetic users to test their glucose frequently. Currently, conventional glucose sensor devices still include manual blood glucose sensors, referred to colloquially as "finger sticks," where users prick an area of their body (typically a finger) to expel a drop of blood that is collected on a sensor test strip that is processed by an electronic unit to perform and analyze an electrochemical test on the sample blood. While finger stick devices have been a reliable tool for diabetic patients for decades, there have been many advancements in developing glucose sensors that function continuously and convey glucose information at discrete intervals to signal display devices, often referred to as "continuous glucose monitors." Such glucose monitors function physically in the causal mode where changes in blood glucose cause changes in tissue sensor signals. However, this mode leads to errors that have historically been difficult to address. This is important, for example, because all clinical decisions about glucose management are based on blood glucose concentrations, not tissue glucose concentrations. As such, conventional glucose sensor devices are substantially prone to errors, and could report inaccurate values that could lead to an unfortunate user decision to act or not act in an appropriate manner.

Disclosed are systems, devices and methods for estimating blood glucose parameters, including blood glucose concentration, from signals of a glucose sensor of various types, such as those that are fully implanted subcutaneously in tissues, inserted percutaneously (through the skin) in tissues, and/or deployed cutaneously (on the surface of skin or tissues), for individuals with diabetes and other medical conditions. The disclosed systems, devices and methods are sometimes referred to herein as "the glucose estimator" or "the estimator" and derivative technologies that are made possible or are made more effective by use of the estimator.

The present disclosure may refer to the following terms according to the corresponding descriptions. These descriptions are not intended to supplant the ordinary meaning or understanding associated with these terms. For example, blood glucose, blood glucose concentration, or true blood glucose, (BG) can refer to concentration of glucose in blood or hematocrit-corrected blood plasma assayed by an accepted reference method. For example, blood glucose concentration reference time-series can refer to blood glucose measurements collected in series at regular or irregular intervals sampled frequently enough to represent actual blood glucose excursions. For example, true blood glucose model can refer to time-series of discrete values of blood glucose concentration, e.g., assayed by an accepted reference method containing interpolated glucose values where certain assayed values are missing. For example, estimated blood glucose concentration, $\overline{BG}$, $YSI_{est}$ can refer to inferred blood glucose concentration, e.g., such as that obtained by implementation of the disclosed estimator. For example, tissue glucose sensor signal, $\overline{ss}$, $y(t)$, $z_k$ can refer to time-series tissue glucose values reported from fully implanted, subcutaneous, or cutaneous sensor. For example, tissue can refer to biological tissues. For example, tissue glucose can refer to averaged glucose concentration in tissues. For example, blood oxygen, or blood oxygen concentration, (BO) can refer to concentration of oxygen in blood that perfuses tissues at the implant site. For example, percutaneous sensor can refer to a type of sensor that remains penetrated through the skin with the sensitive end of the sensor located in tissue, and the signal communication means on, or external to, the surface of the body. For example, cutaneous sensor can refer to a type of sensor in the form of a patch, tattoo, wristwatch or other such means placed directly on the body surface. For example, implanted sensor can refer to a type of sensor and/or signal conveyance means (telemetry) implanted fully in tissue, fully implanted sensor and external telemetry/power conveyance means, and/or implanted percutaneously as a needle or cannula through the skin. For example, measurement error, oxygen measurement error, O can refer to recorded error due to variations in tissue oxygen and perfusion of the local vasculature at the implant site. For example, process error, glucose diffusional lag error, L can refer to error due to glucose diffusion to the sensor and reaction-diffusion within the sensor. For example, random error, w can refer to uncorrelated error, white noise. For example, residual error $\hat{x}(t)$, $\hat{x}_n$, $\hat{x}$ can refer to error remaining after subtraction of measurement error, process error and random error from the composite error or from the sensor signal. For example, composite error can refer to combined time-series error containing measurement error, diffusion process error, random noise error, and residual error. For example, passthrough or "passthru" can refer to residual oxygen flux not consumed in the enzymatic glucose reaction. For example, zero glucose-passthru can refer to maximal pass-through when glucose is absent. For example, Nyquist blood glucose sample interval can refer to the maximal allowable interval between regular blood glucose samples needed to reconstruct blood glucose excursions. For example, unmatched temporal sampling error, alias error can refer to error due to differences or misalignment in reporting rate from the tissue glucose sensor and the regular or irregular sampling rate of the reference blood glucose.

Present methods of glucose monitoring. There are several methods for monitoring glucose in diabetes. Blood samples can be collected by phlebotomy and glucose assayed by a commercial benchtop analyzer, but this approach is not adequate or practical for daily blood glucose management. Another conventional method for glucose monitoring involves collection of a mixture of capillary blood and tissue fluids by finger prick, or "finger-sticking," followed by assay using a portable glucose-sensitive strip reader device. Although widely used, this approach has several disadvantages, including that it is inconvenient, painful, often inaccurate, dependent on user initiative, and is not performed regularly or frequently enough by users to follow typical changes in blood glucose concentration. Another conventional method is assay of glycosylated hemoglobin, $Hb_{A1c}$, which is present in red blood cells. This method requires blood collection and is an indicator of averaged glucose control over the 90-day red blood cell lifetime, but is not useful for daily glucose adjustment.

Several types of implantable and superficial glucose sensors are available or in development, which are intended to monitor and report glucose concentration discretely or continuously. One such glucose sensor is in the form of a needle or is inserted using a needle-like introducer and resides in subcutaneous tissues percutaneously (through the skin) for periods of several days before routine replacement. Another type of glucose sensor is deployed on the surface of the skin (cutaneously) in the form of an adhesive patch, tattoo or wristwatch. Another continuous glucose sensor is fully implanted (subcutaneously) for much longer periods, using some form of telemetry system to convey the signals externally. In all cases, the subcutaneous, percutaneous, and cutaneous placement sites are used rather than an intravascular implant site for reasons of safety and convenience, and to avoid blood clotting or vascular damage.

Tissue glucose concentration. In all cases, glucose sensors that are implanted subcutaneously, percutaneously, or deployed cutaneously report "tissue glucose" concentration, rather than "blood glucose" concentration. In subcutaneous tissues, glucose is metabolized by cells, and is found in the interstitial fluid between cells and in the blood plasma that perfuses microscopic blood vessels in tissues and communicates with interstitial fluid. There is no static or dynamic reference standard for tissue glucose concentration.

Blood glucose concentration, not tissue glucose concentration, is used in all clinical decisions. All clinical decisions, whether made by professional caregivers or by individuals with diabetes themselves, are based on blood glucose concentration, rather than tissue glucose concentration. Conventional tissue glucose sensor devices measure glucose concentration in tissue and relate the measured glucose values to blood glucose concentration for the sensor device's reported values provided to the user. As such, conventional tissue glucose sensor devices are prone to significant errors and could report inaccurate values that could lead to an unfortunate user decision to act or not act in an appropriate manner.

Previous attempts to correlate blood and tissue glucose. In order to use signals from tissue glucose sensors for blood glucose management, existing glucose sensor technologies have employed various forms of correlation between the tissue sensor signals and reference blood glucose values, as a means of surmising blood glucose concentration from the sensor signals. For example, so-called error grid plots are widely used graphical correlations, where the blood glucose or finger-stick reference values are indicated on the horizontal axis and the corresponding sensor glucose value are shown on the vertical axis, with points compared to an equivalence line. The clinical significance of each point depends on which of several graphical regions the point lies, with the goal of avoiding regions that dictate inappropriate clinical actions (e.g., administration of insulin during hypoglycemia). Other versions of error grid plots assume a constant, fixed (non-dynamic) lag between the paired reference and sensor values.

As a result of measurement error, dynamic lag error, and random error, which are present in sensor signals but not part of reference blood glucose, graphical correlations typically have substantial dispersion thereby reducing the accuracy and effectiveness of such methods.

Limitations of conventional methods for relating tissue glucose to true blood glucose. Correlational methods, whether graphical or statistical, have three fundamental limitations when applied to dynamic glucose sensor data. First is the inability to account for the measurement errors, dynamic diffusional lags, and random errors that are present in sensor signals but absent from reference blood glucose values. For example, dynamic diffusional lags are due to diffusion of glucose within tissues, and are present in dynamic glucose recordings, but are not present in static reference glucose values. The inability to separate the temporal components due to dynamic lags from the concentration-dependent components of the signal results in a key source of unaccounted inaccuracies in correlational methods. Second, certain common statistical methods, which rely on averages of data, do not preserve the sequence or time-series relationships of individual data points, and are intrinsically unable to account for dynamic glucose variations.

Causal and anticausal signal modes. The third fundamental limitation is that correlational methods intrinsically cannot distinguish between physical cause and effect. The questions, 'do tissue sensor signals cause blood glucose changes?' or 'do blood glucose changes cause tissue sensor signals?', cannot be resolved by correlational methods (note, the latter question is the correct one.) Glucose sensors operate in the causal mode where blood glucose, BG, causes and precedes glucose diffusion within the tissue to the sensor to produce the sensor signal, SS. Also, the sensor mechanism is based on diffusion of glucose, which, proceeds spontaneously from a source to a drain, rather than the opposite.

FIG. 1A shows a diagram depicting causal mode of glucose sensors. In this model, a glucose sensor 106 is implanted into tissue 104 of a patient or deployed on the surface of the tissue 104. The patient's blood glucose (BG) diffuses into the tissue 104, and the sensor 106 is capable of detecting tissue glucose in the tissue 104 that is produced by the glucose sensor 106 as a sensor signal (SS).

In contrast, practical clinical applications of sensor signals require information processed in an anticausal mode, in which tissue sensor signals are used to infer or estimate blood glucose, $\overline{BG}$. This distinction is important, for example, because all clinical practice decisions in diabetes are based on blood glucose concentration, which is causative, rather than on tissue glucose concentration reported by sensors, which is the effect.

Figure 1B:
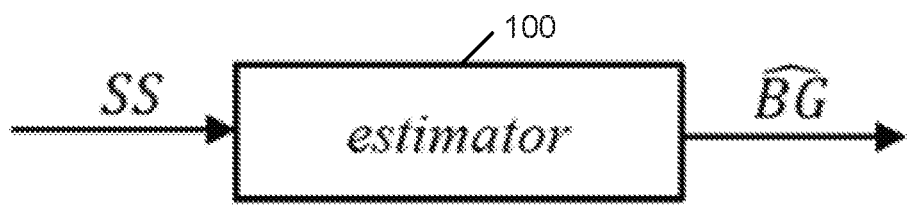
FIG. 1B shows a diagram depicting an example approach using the anticausal mode of estimating blood glucose from a tissue glucose sensor signal in accordance with the disclosed technology.

FIG. 1B shows a diagram depicting an example estimator in accordance with the present technology to process glucose sensor signals in an anticausal mode. In this model, the sensor signal (SS) produced by the glucose sensor 106 corresponding to the detected tissue glucose in the tissue 104 is provided to a glucose estimator 100. The glucose estimator 100 operates in an anti-causal mode, in which tissue sensor signal (SS) is processed to produce serial estimated values of the actual blood glucose concentration of the patient at the corresponding epoch in time when the tissue glucose was measured by the glucose sensor 106.

Historic problems of accuracy of anticausal signals. Presently, continuous, dynamic glucose sensor data is not used in the anticausal mode, even though this would be a significant advantage in the management of diabetes. This is because tissue glucose sensor operation is analogous to anticausal relationships in general engineering practice, which for decades has been known to be notably problematic. Accurate estimation of the input is not feasible by simply using signals in the reverse (anticausal) direction to determine input, because cumulative errors accumulate to a much greater extent in the reverse direction, leading to substantial error in the estimate.

In the 1940's, an improvement in analyzing anticausal data was proposed, known as Wiener-Kolmogorov filtering, which incorporates probabilities of error. However, this approach produces only marginal improvements in estimation accuracy and is presently rarely used. The development of state estimators in the 1960's such as the Kalman, $H_\infty$, and others, in which measurement, processing, and random errors and their statistical probabilities are disentangled and individually subtracted, have been shown to be effective in substantially reducing estimation inaccuracy in anticausal applications. Notably, these and other anticausal analysis models are able to account for the behavior of the physiological parameters that affect glucose concentration measurements in tissue based on the actual blood glucose of the patient. As such, development and implementation of estimators for tissue glucose sensing in which such errors are subtracted requires innovative insights about both the sensor and estimator function.

Example embodiments and example implementations of the anticausal glucose sensing estimator 100 for estimating blood glucose concentration from signals of tissue glucose sensors are described herein. Beforehand, some examples of tissue glucose sensors are discussed below.

Types of tissue glucose sensors. The disclosed estimator 100 can be implemented to determine blood glucose parameters, such as blood glucose concentration, using signals from existing types of tissue glucose sensors. A brief discussion of some types of tissue glucose sensors, including their limitations, is presented herein.

For example, one class of tissue glucose sensors is based on a membrane containing immobilized glucose oxidase coupled to respective electrochemical detectors, which enzyme catalyzes the following reaction:

$$\text{glucose} + O_2 + H_2O \rightarrow \text{glucono-}\delta\text{-lactone} + H_2O_2 \qquad (\text{Eq. 1})$$

Glucose and oxygen diffuse from capillary blood through local tissue to the sensor, where the reaction occurs.

In this type of sensor, for example, the electrochemical detector responds to hydrogen peroxide, the product of the enzyme reaction, to produce a signal current that is largely dependent on glucose, but also affected by oxygen availability from the tissue. This sensor is hereafter referred to as the peroxide-based glucose sensor. The sensor is typically implemented in the form of a needle or is inserted percutaneously using a needle-like introducer, and is intended for short-term (days to weeks) percutaneous implant applications. Also, this type of sensor may require frequent recalibration by reference to glucose finger-stick values. This sensor does not include a reference oxygen sensor for real-time measurement of tissue oxygen, but statistical descriptions of independently determined oxygen measurements can be used, albeit with less accuracy.

Figure 2:
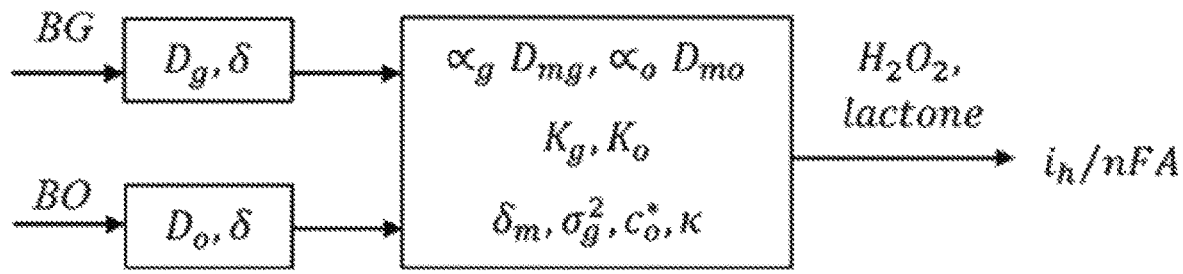
FIG. 2 shows a model of an example peroxide-based glucose sensor.

FIG. 2 shows a detailed model of an example peroxide-based glucose sensor. In peroxide-based glucose sensors, two inputs (blood glucose (BG) and blood oxygen (BO)) diffuse into the tissue space where a sensor electrochemically detects hydrogen peroxide produced as a product of the enzyme reaction shown in Eq. 1. Lactone is an incidental product and the signal or current density is $i_h/nFA$. The essential model parameters are: $D_g$ and $D_o$ the diffusion coefficients of glucose and oxygen in tissues, respectively; $\delta$ the substrate solubility coefficient in tissues; $\alpha_g$ and $\alpha_o$ the respective partition coefficients in the sensor membrane; $D_{mg}$ and $D_{mo}$ the respective diffusion coefficients in sensor membrane; $K_g$ and $K_o$ the respective enzyme Michaelis constants and their ratio $\kappa$; $\delta_m$ the membrane thickness; $\sigma_g^2$ the ratio of enzyme reaction to diffusion in the membrane; and $c^*_o$ the ratio of oxygen to glucose in the membrane.

In another type of tissue glucose sensor, for example, the reaction of Eq. (1) is also the basis of oxygen-based glucose sensors, but this sensor may additionally contain the enzyme catalase, which catalyzes the oxidation of hydrogen peroxide according to the reaction:

$$H_2O_2 \rightarrow \tfrac{1}{2}O_2 + H_2O \qquad (\text{Eq. 2})$$

When catalase is present in excess, the overall reaction becomes:

$$\text{glucose} + \tfrac{1}{2}O_2 \rightarrow \text{glucono-}\delta\text{-lactone} \qquad (\text{Eq. 3})$$

In this sensor, one-half mole of oxygen is consumed per mole of glucose. Residual oxygen not consumed by the enzyme reaction produces a glucose-dependent oxygen flux, or oxygen pass-through (passthru), which is detected by an oxygen detector such as an oxygen-sensitive electrode. The complete sensor in this case also includes a reference oxygen electrode to detect the background tissue oxygen not involved in the reaction. The reference oxygen electrode is specific to oxygen and does not respond to glucose.

Figure 3:
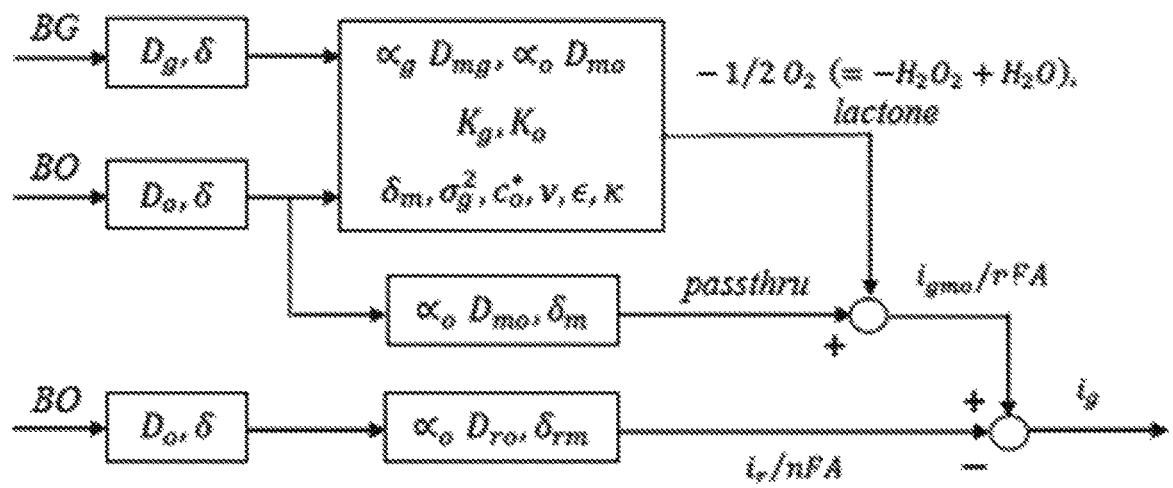
FIG. 3 shows a model of an example differential oxygen consumption-based glucose sensor.

FIG. 3 shows a detailed model of an example differential oxygen consumption-based glucose sensor. The additional model parameters are: $v$ the stoichiometric coefficient, $\in$ a dimensionless geometry parameter, $D_{ro}$ the diffusion coefficient of oxygen in the reference oxygen sensor membrane, and $\delta_{rm}$ the membrane thickness of the reference oxygen sensor. The glucose modulated signal current density of the glucose electrode is $i_{gmo}/nFA$, the reference oxygen signal of the oxygen reference sensor is $i_r/nFA$, and the difference between the glucose electrode and oxygen reference electrode is $i_g$.

With matched fabrication and sufficiently close colocation of the two electrodes at the implant site, the reference oxygen electrode signal can serve either as a dynamic model of the zero-glucose oxygen pass-through of the glucose electrode signal, or function as a real-time indicator of the of actual oxygen measurement error. The pass-through is maximal when glucose is absent, and minimal or zero at high glucose concentration, demonstrating an inverse relationship between pass-through and glucose concentration. The difference between the zero-glucose pass-through oxygen current and the reference oxygen sensor current can be near-zero for closely matched electrodes, as determined in the factory. This sensor type is referred to as the differential oxygen consumption-based glucose sensor.

Table 1 shows a summary of the signal components of the differential oxygen consumption-based glucose sensor.

TABLE 1

| Glucose electrode signal comprises: | Oxygen electrode signal comprises: | Difference signal comprises: |
|---|---|---|
| Reference blood glucose | — | Reference blood glucose remaining |
| Glucose diffusional lag L | — | Glucose diffusional lag L remaining, subtractable |
| Passthru oxygen diffusional lag | Membrane oxygen diffusional lag | Passthru oxygen diffusional lag ≅ Membrane oxygen diffusional lag → Negligible difference remaining |
| Tissue oxygen, oxygen diffusional lag | Tissue oxygen, oxygen diffusional lag model | Measurement error O, subtractable |

A third type of tissue glucose sensor, for example, is the cutaneous glucose sensor used in contact with the skin. These sensors detect glucose in sweat or extruded bodily fluids, take the form of patches, skin paints, tattoos, wrist watches, and similar configurations, and are based on various glucose detection mechanisms, including those described above.

A fourth type of tissue glucose sensor, for example, does not involve enzymes, rather functions by diffusion of glucose into the sensor body and binding or formation of a chemical complex between diffused glucose and a binding agent contained within the sensor body, which complex formation produces a characteristic optical or electrochemical signal. This type of sensor is referred to as the complex-based glucose sensor, and may be implemented subcutaneously, percutaneously or cutaneously. This type of sensor does not typically include a reference oxygen sensor and cannot, therefore, directly account for measurement error due to variable perfusion of the tissue microcirculation which affects glucose transport to the sensor, but can still potentially benefit from removal of process error and random error.

As mentioned above, each of these types of tissue glucose sensors do not measure blood glucose directly and are thereby prone to errors that can result in reporting inaccurate values to the patient user.

Example embodiments of the estimator. The disclosed estimator 100 can be implemented continuously, in which the estimator operates on uninterrupted sensor signals and simulations of uninterrupted signals, in discrete-time, as a discrete-time simulator and simulations of discrete-time where time-series sensor signals are available at regular intervals, and in real-time where continuous and discrete sensor signals are generated in actual time. Example embodiments of the estimator 100 are described below in further detail.

Figure 4:
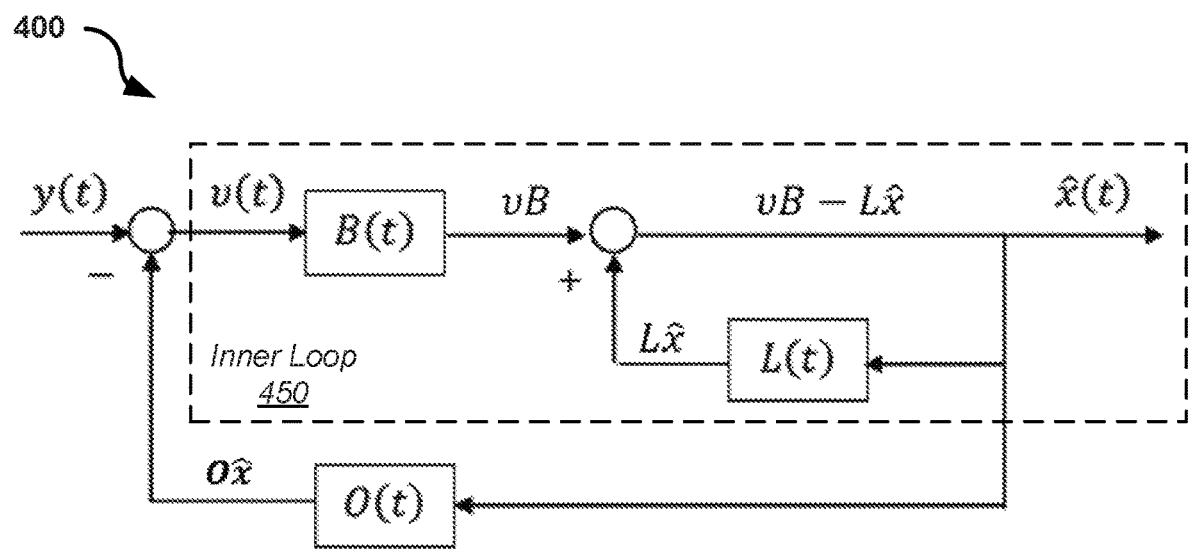
FIG. 4 shows a diagram of an example embodiment of a glucose estimator in accordance with the present technology capable of estimating blood glucose values from a tissue glucose sensor signal.

FIG. 4 shows a diagram illustrating an example embodiment of the estimator 100 in accordance with the present technology capable of estimating blood glucose values from a tissue glucose sensor signal, labeled as estimator 400 for the embodiment in FIG. 4. The estimator 400 includes an outer negative feedback loop that combines an input signal y(t) (e.g., which can include time-series of glucose values of (i) regularly conveyed tissue glucose sensor electrode values, (ii) matched telemetered reference oxygen electrode values, and/or (iii) matched reference blood glucose concentration values) with the negative values of a measurement error, O(t), of the estimator. The estimator 400 includes an inner feedback loop, labeled 450, in which the result of the outer negative feedback combination, υ(t), can be amplified at B and combined in at a positive feedback loop that combines the amplified signal with a glucose diffusion lag function, L(t), to generate the output of the estimator, x̂(t). In implementations, for example, the estimator 400 is initiated by specifying an initial value (not shown) of x̂(t). The estimator 400 and example implementations of the estimator 400 are further described below.

Figure 5:
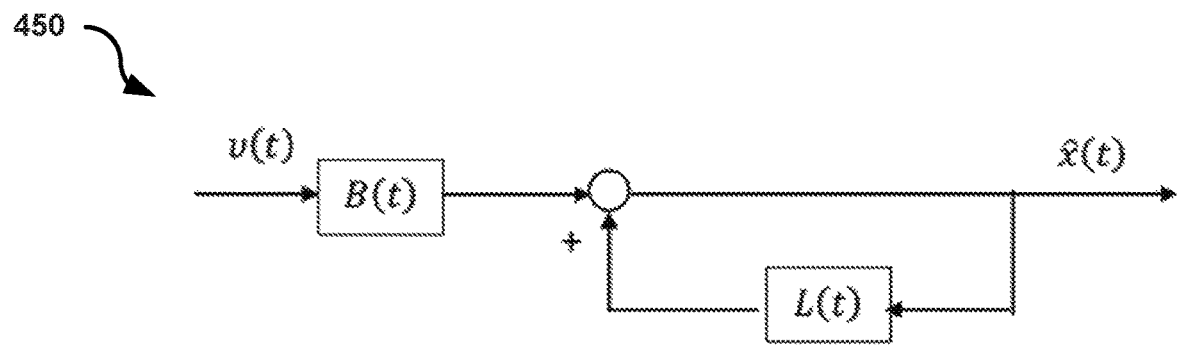
FIG. 5 shows a diagram of the inner loop of the example estimator in FIG. 4.

FIG. 5 shows a diagram of the inner loop of the estimator 400 representing the subtraction of glucose lag error. The inner loop 450 of the estimator 400 adjusts the amplified output, υB, of the combined input signal (y(t)−Ox̂) with the glucose diffusion lag error (Lx̂). v(t) is the time-dependent difference between the input y(t) and the negative-feedback measurement error O(t) or its measured or statistical equivalent. The residual error L(t) is the sum or negative difference between the positive-feedback glucose diffusion lag error L(t) and the relative gain B(t), which can be iteratively adjusted to balance the relative measurement and lag errors to reduce the residual error as desired.

Figure 6:
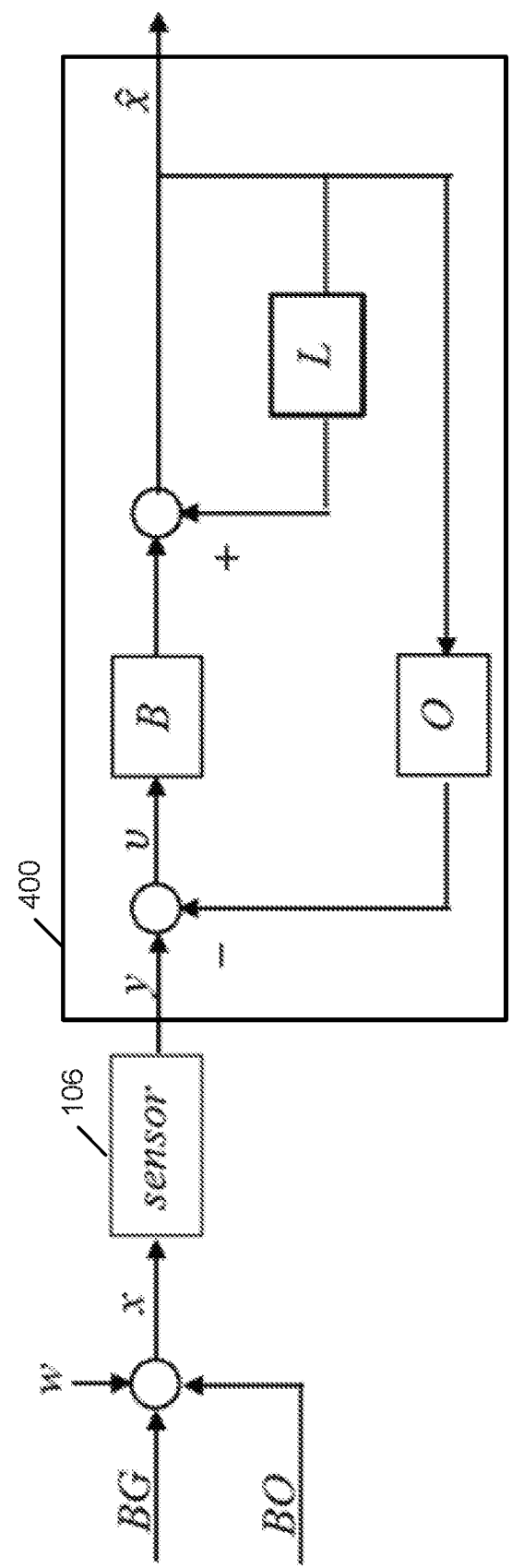
FIG. 6 shows a diagram illustrating an example model of a glucose sensor and estimator in accordance with the present technology.

FIG. 6 shows a diagram of a lumped model of the sensor 106 connected to the estimator 400. The diagram depicts blood glucose (BG), blood oxygen (BO), and random input (w), combined as input (x) into the glucose sensor 106, e.g., which can be implemented with a regularly switched or continuous time-dependent output (y) from the sensor 106 to the estimator 400.

Mathematical description of the estimator. As an example, a discrete-time implementation of the estimator 400 is summarized in the following equations:

$$\dot{\hat{x}}_k = L_k \hat{x}_{k-1} + B_k(i_{g_k} - O_k \hat{x}_{k-1}) + w \quad \text{(Eq. 4)}$$

$$\hat{x}_k = \Psi_k \hat{x}_{k-1} \quad \text{(Eq. 5)}$$

$$\hat{x}_{k-1} = \hat{x}_0 \quad \text{(Eq. 6)}$$

where, the first equation (Eq. 4) is a basis equation for the estimator 400 with previously described terms expressed in series notation; the second equation (Eq. 5) is the iteration operator that creates the time series; and the third equation (Eq. 6) is the initial value specified by a user, for example. The terms in the equations above are as follows.

Measurement error, O, or oxygen measurement error, shown in Eq. 4, is due to dynamic variations in background tissue oxygen and variations in microvascular perfusion of local tissues, which affect access of both glucose and oxygen. Enzyme-based sensors are further affected by oxygen measurement error, as oxygen variations affect the enzyme reactions, in the following respective ways.

For the peroxide-based glucose sensor, measurement error is due to tissue glucose and tissue oxygen variations, which modulate the enzyme reaction and therefore affect the production of the peroxide product. There is no direct means of detecting or dynamic modeling the measurement error in the peroxide-based glucose sensor, as there is no reference oxygen sensor in peroxide-based glucose sensing, but a statistical approximation of the measurement error from independent tissue oxygen sensor recordings may be used, albeit with reduced accuracy.

For the differential oxygen consumption-based glucose sensor, measurement error is based on local tissue glucose and oxygen concentration and variable perfusion of the local vasculature. Tissue oxygen variations continuously determined by the oxygen reference electrode signal can serve to model of the effects of oxygen in the glucose electrode, as summarized in Table 1.

As the signal of the oxygen reference sensor may be reported in various units, such as, for example, current density, oxygen flux, or tissue oxygen partial pressure, which units may be different from units used to report the glucose sensor signal, the gain and offset of the reference oxygen signal may be adjusted by iteration to obtain acceptable accuracy of the measurement error.

For complex-based glucose sensors and other sensors that do not rely on oxygen for glucose detection, measurement error is due to variations in perfusion of local tissues that affect the delivery of glucose from tissues and therefore affect glucose measurement accuracy. Measurement error may be approximated by statistical oxygen variations from independent tissue oxygen sensor recordings, albeit with reduced accuracy.

Process error, L, or glucose diffusion lag error, shown in Eq. 4, is determined by the rate and direction of change of blood glucose and is a variable lag that is part of the sensor dynamic response but not part of the reference glucose or true blood glucose model. The diffusional lag error is determined by the rate and direction of change of blood glucose. This error can be modeled as a first-order lag, first-order lag with delay due to circulation from the reference sampling site to the implant site, or as a second-order delay, and corresponds to physical aspects of mass transfer in tissue. This error can be substantial and, when unaccounted for, is a major cause of poor correlation between sensor signals and blood glucose.

The form of L can be approximated as a first-order lag when diffusion is much slower than convection, and expressed in the time domain as $$\frac{d}{dt}(e^{-\tau_g}),$$

where the derivative $$\frac{d}{dt}$$

is a component of the discrete estimator and is taken at successive sampling instants and $\tau_g$ is the inverse of the first-order lag time-constant. The Laplace transform, $\mathcal{L}$, of the time-domain expression, $$\mathcal{L}\left[\frac{d}{dt}(e^{-\tau_g})\right] = \frac{-K_g}{(1+\tau_g s)},$$

gives an equivalent expression in the Laplace domain, which is $$\frac{-K_g}{(1+\tau_g s)},$$

where the Laplace variable is s and the gain $K_g$. The gain $K_g$ and offset can be adjusted by iteration to obtain acceptable accuracy of the residual error. The equivalent expressions for the glucose diffusion lag are convenient for interchange between continuous and discrete implementations of the estimator 400.

In some implementations, for example, a method for estimation of the numerical value of $\tau_g$ in L includes executing one or more iterations of the estimator 400 to minimize the residual error based on estimated diffusion coefficient and diffusional distance for glucose in tissues. For example, the value of $\tau_g$ can be estimated empirically as 6.9 minutes, and, $e^{-\tau_g}=e^{-1/6.9}=e^{-1.45}$ for the sample data associated with human subject S1:C6 discussed below with respect to FIGS. 9A-9C.

Random error, w. Random error, also referred to as noise, is independent of concentration and frequency. This type of error, while present in all signals, may be averaged by the much slower, discrete signal reporting cycle in the disclosed estimator system, for example, and may be insignificant.

Residual error, x̂. Residual error is the combined mismatch between the above errors, and represents the only unresolved error in the glucose signal after application of previous components of the estimator 400. The residual error can be further reduced by iterative improvement in the accuracy of the measurement, process, and random errors prior to their subtraction.

Estimation of B. The parameter B represents the relative strength of the glucose diffusion lag error to the oxygen measurement error. In some implementations, the parameter B can be adjusted by iterations in a trial-and-error substitution process for maximizing the accuracy of the estimator 400, as shown in Table 2, for example, by iteration to minimize the residual error. Alternatively, for example, an expression of the estimator 400 can be rewritten as $$\frac{(\hat{x}_k - L_k \hat{x}_{k-1})}{(i_{g_k} - O_k \hat{x}_{k-1})} = \frac{\lambda_k}{\upsilon_k} = B_k \quad \text{(Eq. 7)}$$

where $\lambda_k$ is the diffusion lag model, $\upsilon_k$ represents the net measurement error, and $B_k$ is written as a time-series.

Composite error. Composite error is the difference between the tissue glucose sensor signal and the reference blood glucose. The composite error is the summation of the measurement, process, random, and residual errors.

Analysis method by initial subtraction of composite error. In some implementations of the estimator 400, the composite error is first determined by subtracting the blood glucose reference from the original tissue glucose signal, then the residual error is determined from the composite error by subtracting the measurement error, the process error, and random error (e.g., if significant), in which residual error is then added back to the reference blood glucose and compared to the original reference blood glucose to estimate accuracy.

Analysis method by direct subtraction of component errors. In some implementations, the measurement error (O), the process error (L), and random errors are first estimated by the estimator 400, then subtracted individually directly from the original tissue sensor signal, e.g., rather than involving the composite error, leaving an estimate of the reference blood glucose plus the residual error, e.g., referred to the estimated reference blood glucose. Subsequently, the estimated reference blood glucose can then be compared to the actual reference blood glucose, e.g., by use of MARD calculation, to estimate accuracy.

In some implementations, a method for estimating the composite error can include identification of a segment of time-series data that rises at a maximal sustained rate equal to rate of rise of the reference glucose, while the oxygen measurement error and glucose diffusion lag error remain near constant. In such a segment, the composite error equals the reference glucose, and measurement, process and residual errors are near zero. An example of this is shown at point 829' around sample points 81-88 in FIG. 8B and at point 839' around sample points 115-120 in FIG. 9B. Notably, such segments are not found in all data sets. For example, such segments provide a means for confirming parameter values of the glucose diffusion lag model.

Assessment of accuracy of the estimator. Assessment of the accuracy requires a means of comparison of estimated glucose values with reference values. A commonly-used, non-graphical parameter for comparison of glucose sensor signals and reference values is the mean absolute relative difference, or MARD, given in units of percent as $$MARD = \operatorname{mean}\left\|\frac{\text{sensor} - \text{reference}}{\text{reference}}\right\| \times 100$$

The values of sensor and reference are conventionally assumed to be matched at the same sampling instant, or provisions for mismatched sample timing described herein apply. Of note is that the terms within the vertical double-bars of Eq. 8, i.e., ((sensor−reference)/reference), are equivalent to the composite error.

Example of discrete-time estimator application. An initial value of $\hat{x}_0$ is posited, multiplied by O and L, where O may include adjusted offset and gain, and L is given in the Laplace form, then value of $\hat{x}_{k-1}$ is calculated by the estimator equation for an initial value of B, and the process repeated to complete the time-series. The value of B may then adjusted by iteration to obtain acceptable accuracy, as described below.

Temporal mismatch between sensor and reference sampling—Adaptation of the disclosed estimator to conventional data collection practices. Although a widely accepted performance criterion, MARD has practical limitations when applied in conventional data collection practices for obtaining time-series glucose data. A fundamental difficulty is that implanted sensors report tissue glucose values continuously or at regular intervals, such as every 2, 3, or 5 minutes, whereas reference blood glucose samples are practically obtained only at greater intervals, such as every 10, 15, 60, or more minutes, or at irregular intervals. There can be a temporal mismatch between the sensor and reference values, in which sensor data is disregarded, or other arbitrary means of matching sensor and reference values are devised to allow calculation of MARD.

Blood glucose excursion reconstructed from temporal matched sample sets. In addition to the composite error and its components, the temporal sampling regime can affect the accuracy of the blood glucose estimate. Temporal matched time-series data is where tissue sensor glucose, oxygen sensor, and corresponding blood glucose reference values are collected at the same regular sampling instant.

Temporal error based on unmatched samples. In practice, however, it is rarely possible to obtain matched time-series sensor and reference blood glucose values because, although sensor time-series values are sampled and reported by telemetry at regular intervals, reference blood glucose values are typically sampled by phlebotomy or finger-stick measurements from the subject at greater, and typically irregular, intervals.

This poses a problem in demonstration of estimator accuracy by MARD or other comparative means. For example, either the unmatched sensor signal values are discarded, and MARD is calculated from intermittent matched sets of sensor signal-glucose reference values, thereby not fully representing the sensor response; or, a means for approximating the reference blood glucose time-series, such as linear interpolation between neighboring measured blood glucose values, is applied, matching reference glucose values to sensor signal values where possible and using interpolated reference glucose values to sensor signal values elsewhere, leading to a closer approximation, the accuracy of which nevertheless depends on the reference blood glucose sampling interval.

In the former, conventional method, referred to as matching by sensor signal depletion, there are insufficient reference blood glucose values to accurately describe the actual excursion, and some sensor signal values are discarded to obtain matching values. This conventional method can result in a MARD value that may seem acceptable, but is actually unrepresentative of both the true blood glucose excursion and the sensor signals.

In an example method in accordance with the present technology, sometimes referred to as the matching by reference signal approximation (with sensor signal preservation), the sensor signal is preserved and accurately represented, in which the reference blood glucose is an approximation, or blood glucose model.

The example method can be implemented based on retaining all glucose sensor signal values and linear interpolation of frequently sampled blood glucose reference values with point-by-point matching, and is further described in the present disclosure. Notably, in some example implementations, the former, conventional method of data matching by sensor signal depletion can also be used with methods for estimation in accordance with the present technology, albeit with poorer accuracy.

Figure 7A:
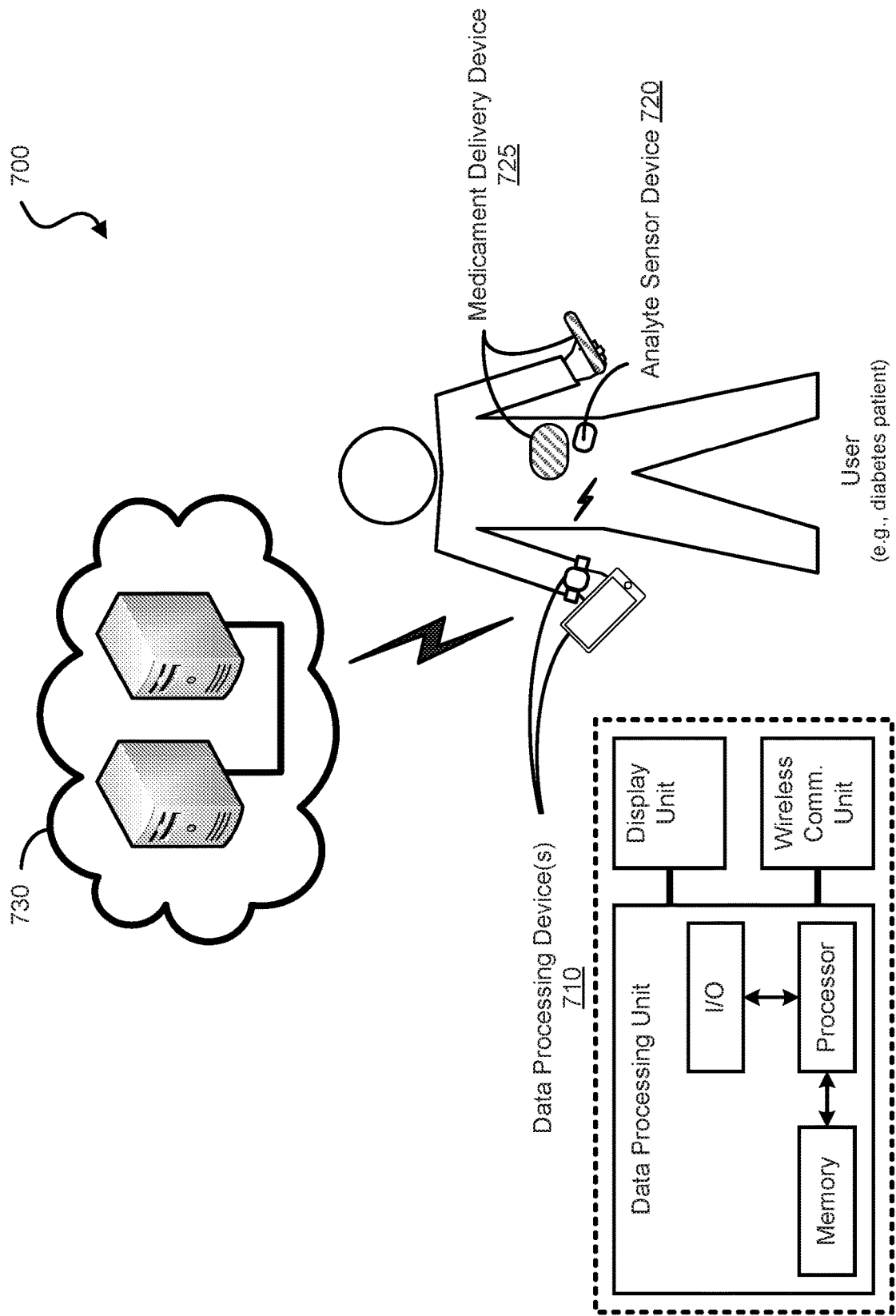
FIG. 7A shows a diagram of an example embodiment of a blood glucose estimation system in accordance with the present technology for estimating blood glucose concentration from signals of enzyme-based and complexation-based glucose sensors.

FIG. 7A shows a diagram of an example embodiment of a blood glucose estimation system 700 in accordance with the present technology for inferring or estimating blood glucose parameters, including concentration, from signals of enzyme-based and complexation-based glucose sensors, which can be implanted subcutaneously in tissues, implanted percutaneously, or deployed cutaneously on individuals with diabetes (e.g., diabetes patient) and other medical conditions. The system 700 includes a data processing device 710 configured to store and operate the estimator 100, including the example embodiment of the estimator 400, which is discussed with reference to FIG. 7A. For example, the estimator 400 can be embodied in a non-transitory computer readable program storage medium having code stored thereon, where the code, when executed by a processor, causes the processor to process instructions for estimating blood glucose concentration according to the disclosed methods of the estimator as described herein.

The data processing device 710 can include a mobile communications device, such as a smartphone, a tablet, and/or a wearable device, like a smartwatch, smartglasses, etc. In some implementations, the estimator 400 can optionally reside and operate on a remote computing device in communication with the data processing device 710, such as on a laptop and/or desktop computer, or network-based server computer. In some embodiments, the system 700 includes one or more computers 730 in communication with other computers and devices in a network, such as over the Internet, referred to as "cloud" system 730. The one or more computers 730 are also referred to as cloud computer(s) or server(s). In such embodiments, the cloud system 730 is in communication with the data processing device 710 to receive, process and/or store data. In some implementations, the estimator 400 can optionally reside and operate on the cloud system 730 in addition or alternatively to residing and operating on the data processing device 710.

In some embodiments, the system 700 can include an analyte sensor device 720 to record analyte data of the user, e.g., glucose. The analyte sensor device 720 is in communication with the data processing device 710, such that the estimator 400 can receive data from the sensor device 720. For example, the sensor device 720 can include an implanted glucose sensor device, percutaneous glucose sensor device, and/or cutaneous glucose sensor device. As depicted in the diagram, the sensor device 720 is a wearable sensor device, such as a continuous glucose monitor (CGM), to obtain tissue or blood glucose measurements that are processed to produce continuous glucose values. For example, the sensor device 720 can include a device that processes, stores and/or displays the glucose data, which can be implemented on a separate stand-alone display device, on the wearable component of the sensor device 720, and/or on the data processing device 710. In some implementations, the sensor device 720 can include an additional sensor device or devices to provide other health metric data, such as other analyte concentration data, heart rate, blood pressure, user movement, or other. In some examples, the additional sensor device can include a reference oxygen sensor for real-time measurement of tissue oxygen. In some implementations, the additional sensor device can include the sensor(s) or other functionalities provided by the data processing device 720 (such as the smartphone and/or smartwatch), including health aggregation apps that aggregate health-related data from other apps and devices on or in communication with the smart device.

In some embodiments, the system 700 can include a medicament delivery device 725 to administer a certain dose of a medicine to the user, e.g., insulin. In such embodiments, the medicament delivery device 725 is in communication with the data processing device 710, such that the estimator 400 can receive and/or transmit data from and/or to the medicament delivery device 725. In some implementations, for example, the medicament delivery device 725 includes an insulin pump, whereas in other implementations, the medicament delivery device 725 includes an insulin pen. In some implementations, for example, the medicament delivery device 725 includes both the insulin pump and the insulin pen for a single user. In some embodiments, the analyte sensor device 720 and medicament delivery device 725 are included in an artificial pancreas system, including a controller in communication with the estimator 400. In such example embodiments, the estimator 400 can be resident on the data processing device of which the controller of the artificial pancreas operates.

As shown in FIG. 7A, the data processing device 710 includes a data processing unit including a processor to process data, a memory in communication with the processor to store data, and an input/output unit (I/O) to interface the processor and/or memory to other modules, units or devices of the data processing device 710 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and/or transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud, such as the example servers 730). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with a wireless communications unit of the data processing device 710 to utilize various types of wired or wireless interfaces compatible with typical data communication standards, for example, which can be used in communications of the data processing unit with other devices such as the sensor device 720, via a wireless transmitter/receiver (Tx/Rx) unit, e.g., including, but not limited to, Bluetooth, Bluetooth Low Energy (BLE), Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the data processing device 710 or an external device.

In some embodiments, for example, the data processing device 710 can include a display unit configured to be in data communication with the data processing unit, e.g., via the I/O, to provide a visual display, an audio display, and/or other sensory display that produces a user interface (such as on a software application) for displaying data associated with the estimator 400. For example, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In implementations of the system 700, for example, the blood glucose parameter estimator is configured to control functionality of the sensor device 720 and/or the medicament delivery device 725. For example, upon implementation of the estimator 400 (e.g., resident on the data processing device 710), the estimated blood glucose values can be provided to a controller unit of the sensor device 720, the medicament delivery device 725, or both, to affect (e.g., cause a change) in operation of the respective device or devices. In some implementations, the estimator 400 can produce a control command, received at the device 725, to cause the medicament delivery device 725 to administer an insulin bolus and/or basal dose. In some implementations, the estimator 400 can provide the estimated blood glucose values, which are processed by the controller of the medicament delivery device 725 to generate the command to administer the insulin bolus and/or basal dose.

In some implementations of the system 700, the estimator carries out a method for inferring or estimating blood glucose concentration from signals of enzyme-based and complexation-based glucose sensors that are implanted subcutaneously in tissues, implanted percutaneously, or deployed cutaneously on individuals with diabetes and other medical conditions includes the following. The method applies to discrete and/or continuous sensor signal values that are conveyed at regular or irregular intervals from subcutaneous implanted glucose sensor systems, signals of percutaneous glucose sensors, and from signals of cutaneous glucose sensor systems.

Figure 7B:
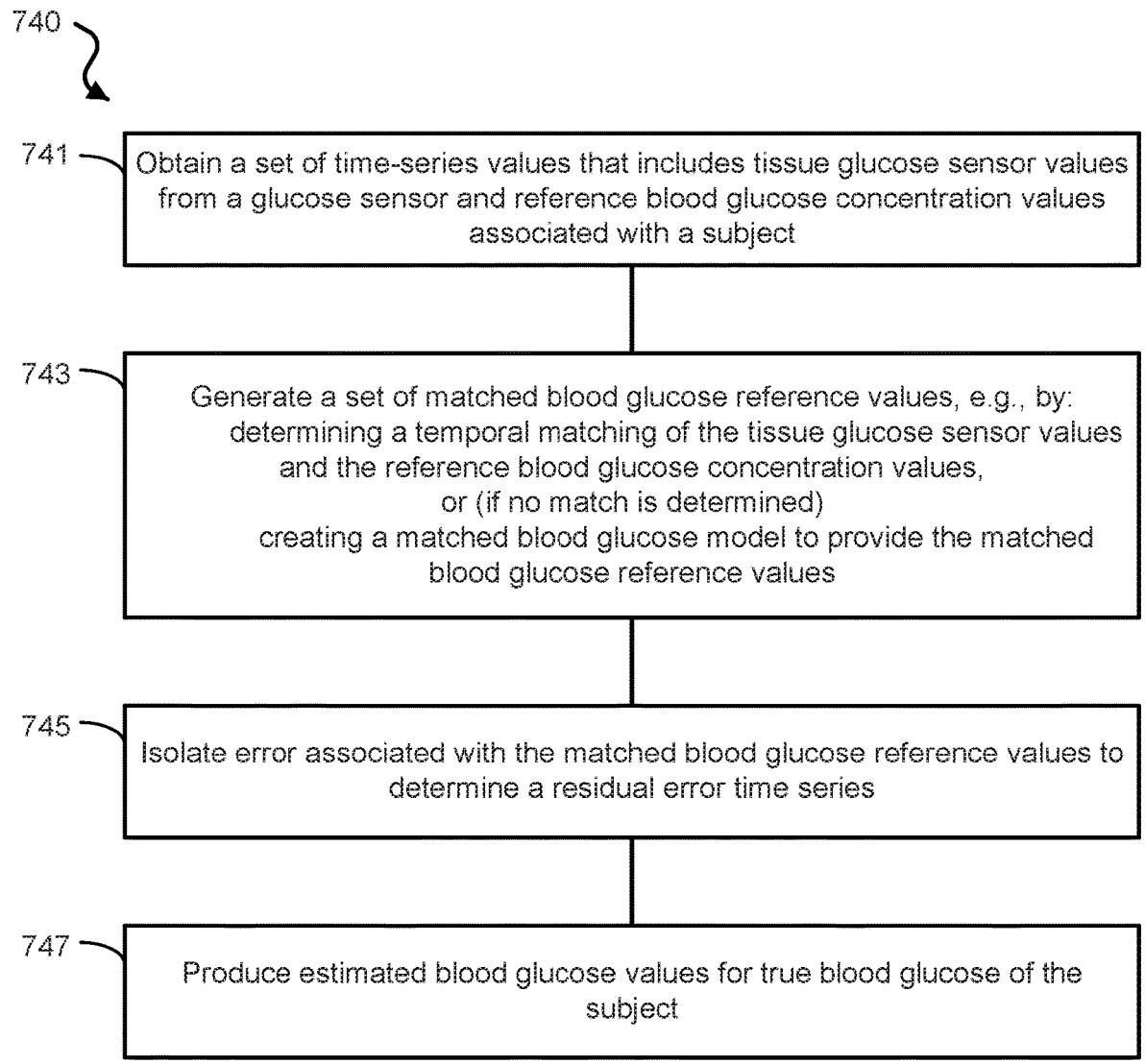
FIGS. 7B-7D show diagrams of example embodiments of methods in accordance with the present technology for estimating blood glucose concentration from signals of glucose sensors.

FIG. 7B shows a flow diagram of an example method, labeled 740, for estimating blood glucose concentration from signals of glucose sensors. The method 740 can be implemented by the example embodiments of the blood glucose estimator described herein, including the estimator 400. The method 740 includes a process 741 to obtain a set of time-series values that includes tissue glucose sensor values from a glucose sensor and reference blood glucose concentration values associated with a subject. In some implementations, the reference blood glucose concentration values include at least three values associated with the subject, e.g., for producing a statistically significant MARD calculation. The method 740 includes a process 743 to generate a set of matched blood glucose reference values by determining a temporal matching of the tissue glucose sensor values and the reference blood glucose concentration values, in which, when no temporal match is determined, the process 743 includes creating a matched blood glucose model to provide the matched blood glucose reference values. The method 740 includes a process 745 to isolate error associated with the matched blood glucose reference values to determine a residual error time series. In some implementations, the isolated error includes an isolated composite error, from which a measurement error can be isolated, a process error can be isolated, and/or a random error can be isolated, to determine the residual error time series. The method 740 includes a process 747 to produce estimated blood glucose values for true blood glucose of the subject. In some implementations, the process 747 includes adding the reference blood glucose concentration values to the residual error time series.

In some implementations of the process 745, for example, isolating the error includes determining the composite error and/or the components including the measurement error, the process error, and the random error individually, by (i)

subtracting the reference blood glucose concentration values from the matched blood glucose reference values to determine the composite error, and (ii) subtracting measurement error from the determined composite error to determine a remainder comprising the process error and random error, and (iii) subtracting the process error and the random error (e.g., if significant) from the remainder to determine the residual error time series.

In some embodiments, for example, the method 740 further includes providing the estimated blood glucose values to a controller associated with an insulin delivery device to affect an insulin delivery control to the insulin delivery device. In some embodiments, for example, the method 740 further includes providing the estimated blood glucose values to a controller associated with the glucose sensor to affect a glucose measurement parameter of the glucose sensor.

Figure 7C:
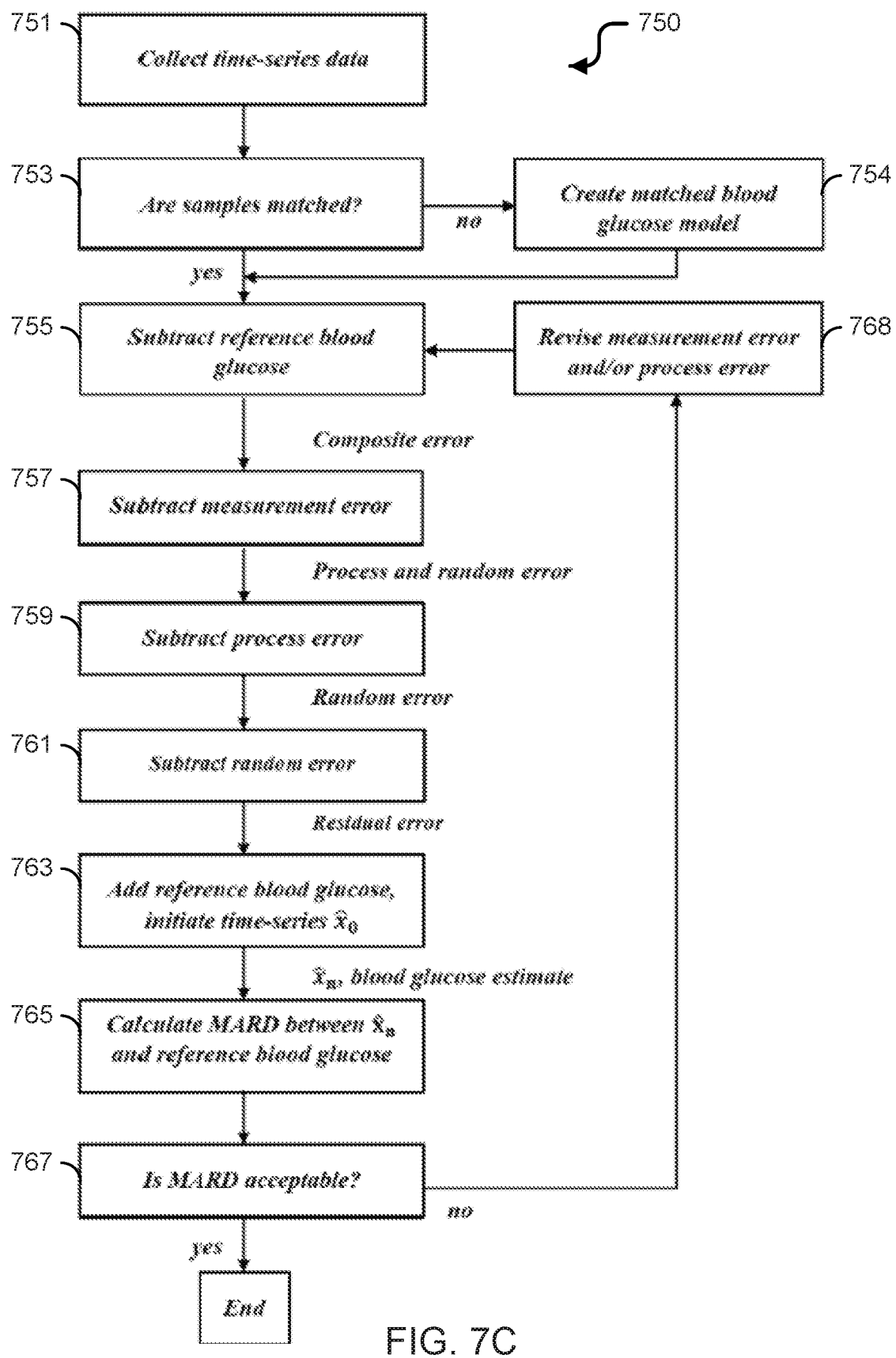

FIG. 7C shows a flow diagram of the method, labeled 750, to implement the estimator for inferring or estimating blood glucose concentration from signals of enzyme-based and complexation-based glucose sensors. The method 750 can be implemented by the example embodiments of the blood glucose estimator described herein, including the estimator 400. The method 750 can be implemented by the system 710. The method 750 includes a process 751 to collect time series data associated with glucose measurements obtained by the glucose sensor. The method 750 includes a process 753 to determine if samples from the time series data are matched, e.g., temporally matched. When the result of the process 753 is unmatched (shown as "no" in the diagram), the method 750 includes implementing a process 754 to create a matched blood glucose model. The method 750 includes a process 755, using the matched samples from the process 753 or matched data from the matched blood glucose model from the process 754, to subtract reference blood glucose values. For example, the process 755 can include subtracting the true blood glucose model values from the matched tissue glucose sensor signal values to produce the time-series composite error. The method 750 includes a process 757 to subtract measurement error from the time-series composite error. The method 750 includes a process 759 to subtract process error from the time-series composite error. In some implementations, the method 750 includes an optional process 761 to subtract random error from the time-series composite error. In various implementations of the method 750, the processes 757, 759 and 761 can be performed in any order to result in the residual error. The method 750 includes a process 763 to add reference blood glucose values to initiate time series to generate the estimated blood glucose concentration of the subject from the glucose sensor data.

In some embodiments, for example, the method 750 can optionally include a process 765 to calculate MARD between the estimated blood glucose concentration values and the reference blood glucose values. In some embodiments, for example, the method 750 can optionally include a process 767 to check/determine that the calculated MARD from the process 765 is acceptable. In some implementations of the process 767, when the MARD is acceptable, the process is complete; and when the MARD is unacceptable, a process 768 is implemented to revise measurement error and/or process error, e.g., by repeating the processes 755-763.

In some implementations of the method 750, the processes 755 to 763 are implemented to identify the respective errors in a data set, and determine the optimal estimator configuration and parameter values to address the errors.

Values for the parameters B, gain, L(t), glucose diffusion lag, and O(t), the error function of the estimator, are determined as shown in FIG. 5. For example, the true blood glucose model reference values are subtracted from the sensor signal to define the composite error. The composite error contains the measurement error, process lag error, random (noise) error, and the residual error, but not the reference blood glucose. These errors are then accounted for individually, in the processes 757, 759 and 761, leading to an optimal time-series estimate for glucose values. The measurement error is removed by a negative feedback loop in a continuous implementation or individual discrete values are subtracted from the composite error. The lag error is then multiplied by the initial value $\hat{x}_{k-1}$ or current blood glucose estimate $\hat{x}_k$ and inserted in a positive feedback loop in a continuous implementation or added individually to values of the residual in a discrete implementation. The value of B is then systematically adjusted if necessary and held constant to adjust the gain on the positive and negative feedback loops to adjust the relative strength of the measurement error compared to the process error. The random error, if present, is estimated and subtracted. To estimate the final accuracy by calculation of MARD, for example, the true blood glucose reference values are then added back to the existing residual and the calculation made.

Figure 7D:
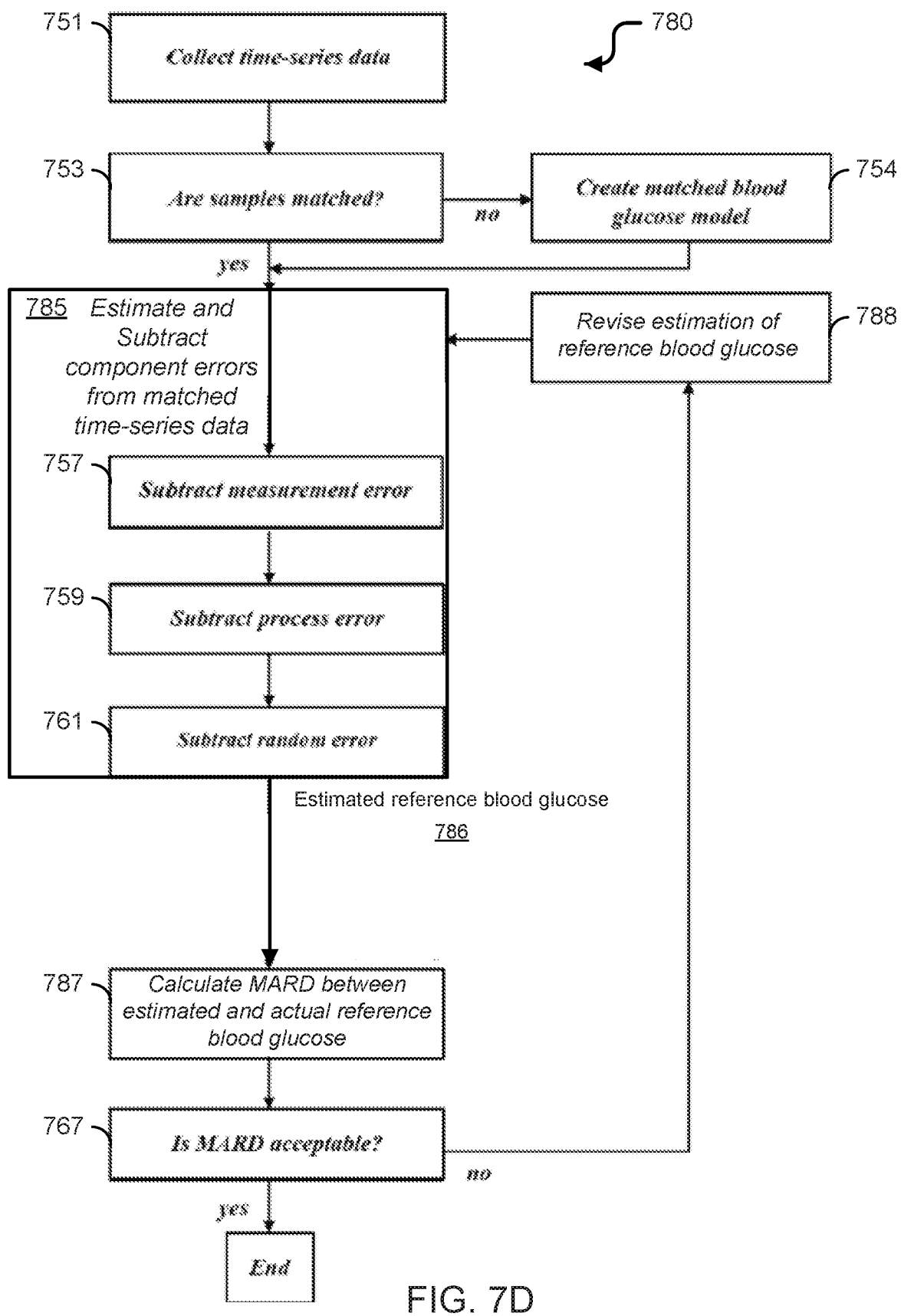

FIG. 7D shows a flow diagram of another method in accordance with the disclosed technology, labeled 780, which can implement the estimator for inferring or estimating blood glucose concentration from signals of enzyme-based and complexation-based glucose sensors. The method 780 includes subtracting the component errors determined by the estimator 400 from the original tissue sensor signal. The method 780 can be implemented by the example embodiments of the blood glucose estimator described herein, including the estimator 400. The method 780 can be implemented by the system 710. The method 780 includes the process 751 to collect time series data associated with glucose measurements obtained by the glucose sensor. The method 780 includes the process 753 to determine if samples from the time series data are matched, e.g., temporally matched. When the result of the process 753 is unmatched (shown as "no" in the diagram), the method 780 includes implementing the process 754 to create a matched blood glucose model. The method 780 includes the process 785, using the matched samples from the process 753 or matched data from the matched blood glucose model from the process 754, to subtract component errors determined by the estimator 400. For example, the process 785 can include determining the measurement error (O), the process error (L), and random errors (e.g., if significant) and then subtracting the determined component errors individually directly from the matched time-series data, which results in an estimate of the reference blood glucose plus the residual error, e.g., referred to the "estimated reference blood glucose" (labeled 786 in FIG. 7D). In various implementations of the method 780, the processes 757, 759 and 761 can be performed in any order to result in the estimated reference blood glucose 786.

In some embodiments, for example, the method 780 can optionally include a process 787 to calculate MARD between the estimated reference blood glucose (concentration values) 786 and the actual reference blood glucose values. In some embodiments, for example, the method 780 can optionally include the process 767 to check/determine that the calculated MARD from the process 765 is acceptable. In some implementations of the process 767, when the MARD is acceptable, the process is complete; and when the MARD is unacceptable, a process 788 is implemented to revise the determinations by repeating the process 785.

The aforementioned methods include various embodiments of the estimator, in which individual sources of error contained in continuous and discrete glucose sensor signals are isolated and minimized to reduce the overall error in estimated blood glucose values. Individual sources of error include: 1) error due to simultaneously or independently measured background variations in tissue oxygen concentration and glucose diffusional lag of the glucose electrode, or are used as an approximation of the oxygen response of the glucose electrode; 2) error due to the glucose diffusional lag, which is large relative to the reaction-diffusion lag of the sensor itself, and therefore dominates the glucose signal; and 3) random error.

For example, some key advantages of the disclosed methods include allowance of estimation of blood glucose values, which are used by caregivers and individuals with diabetes to make decisions about application of therapy from signals of glucose sensors. Although glucose sensors function in a causal mode where changes in blood glucose cause changes in tissue sensor signals, the method functions in the anti-causal mode, in which tissue sensor signals lead to continuous or discrete estimates of blood glucose concentration. This is an alternative to present conventional methods of characterization of sensor accuracy by correlational methods, which are unable to account for dynamic components of the signal including measurement error, process error, random error components and residual error, and are of limited accuracy.

In some embodiments, methods for determining parameter values of the estimator are described, in which the parameter values can be used in operations of the estimator. Also described are methods for continuous, discrete-time and/or real-time operation of the estimator. Also described is the use of blood glucose estimates determined by the estimator to predict future blood glucose estimates ahead of present values. Also described are techniques for extending the sensor response to the full dynamic range of biological glucose excursions of individuals with diabetes. Also described are techniques for estimating sampling errors in sensor operation. Also described are example applications of the disclosed systems, devices and methods that provides improved accuracy over existing signal interpretation methods based on correlation between blood glucose concentration and sensor signals. The disclosed estimator can be used to affect methods of diabetes therapy based on estimated blood glucose values.

Figure 8A:
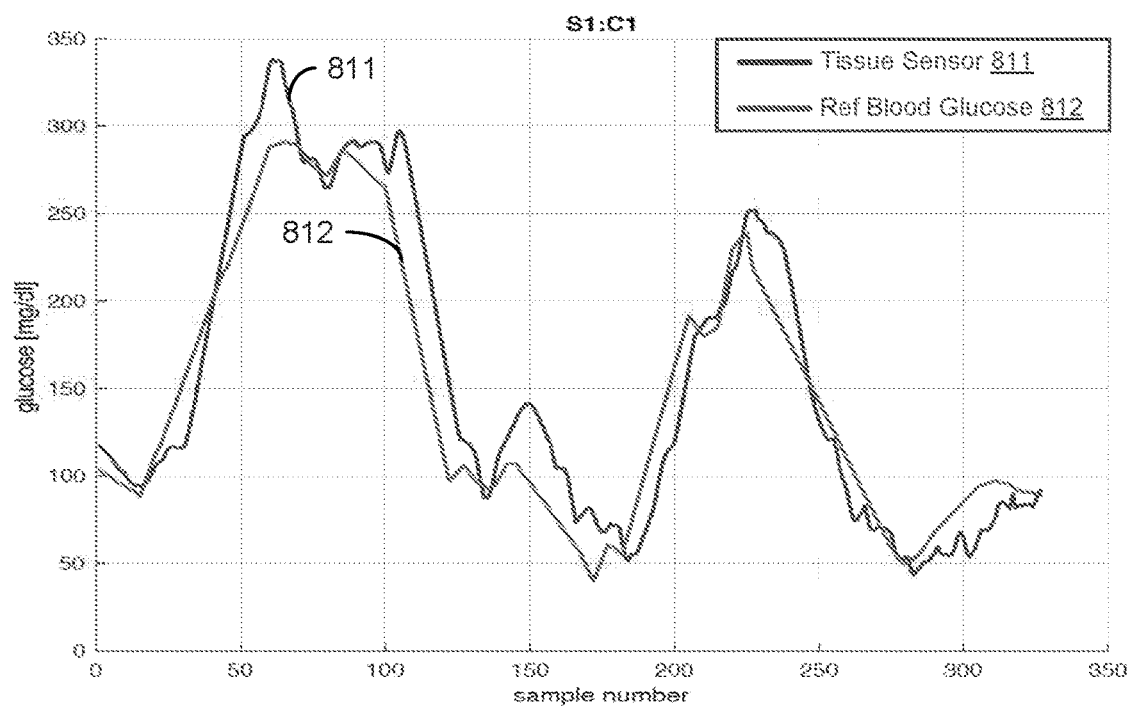
FIGS. 8A-8C show data plots depicting example results from an implementation of an example estimator in continuous mode for a first subject.
Figure 8B:
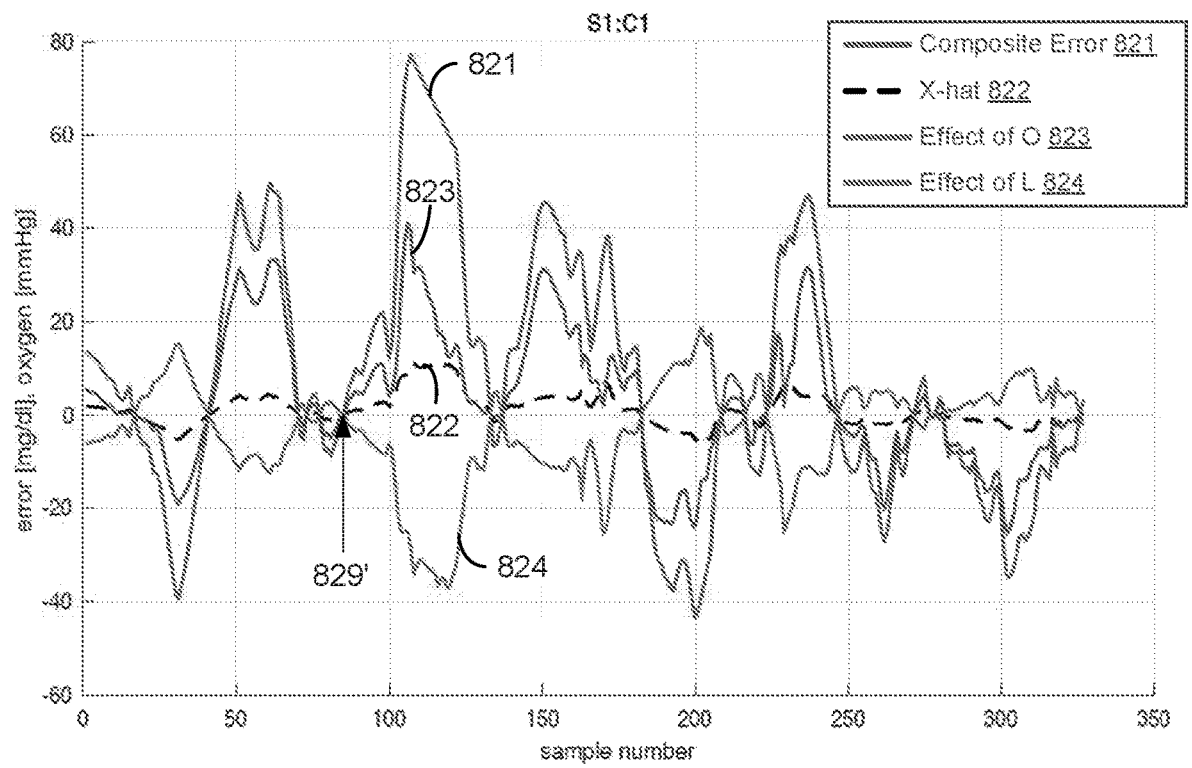
Figure 8C:
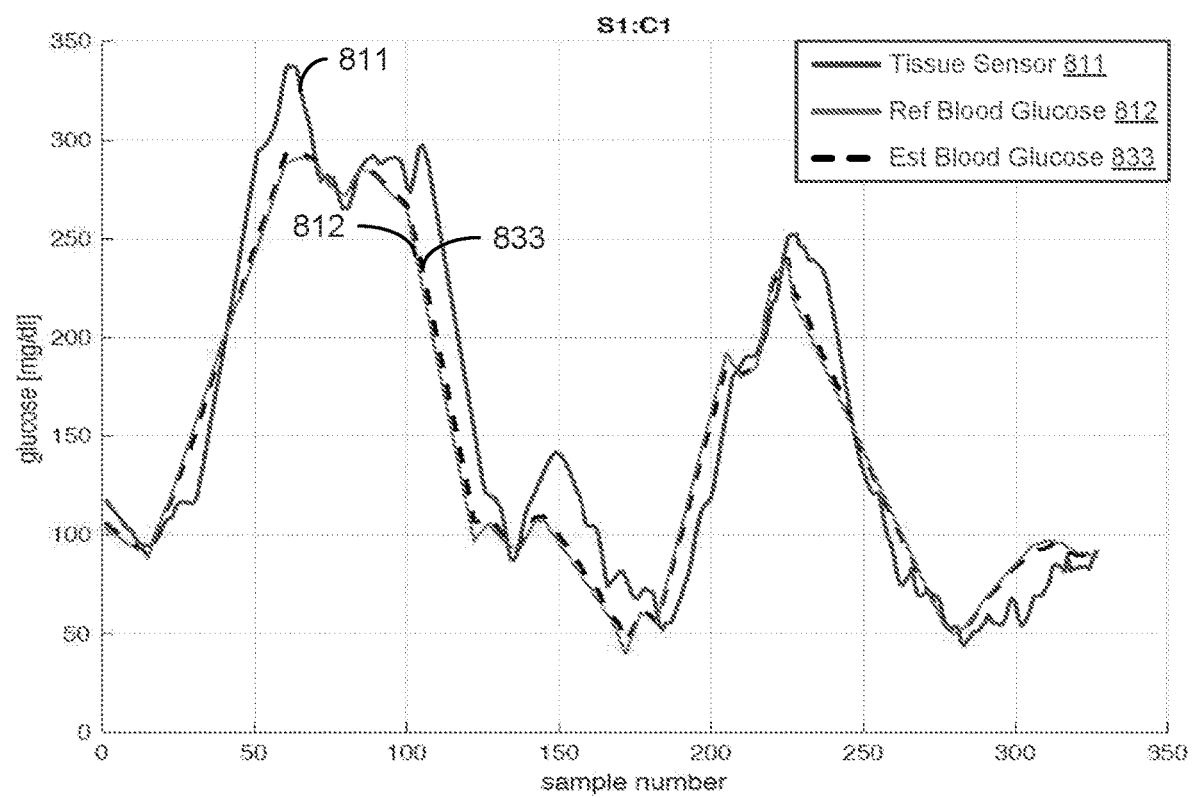

Example implementations of continuous blood glucose estimation. Example implementations of the method 750 and system 700 were performed. Example results from such implementations using the disclosed estimator are shown in FIGS. 8A, 8B and 8C for a first test subject (referred to as subject S1:C1), and in FIGS. 9A, 9B and 9C for a second test subject (referred to as subject S1:C6). The example implementations include time-series data obtained from a differential oxygen consumption-based glucose sensor with battery-operated telemetry system implanted subcutaneously in the human diabetic subjects under an FDA-approved protocol.

Figure 9A:
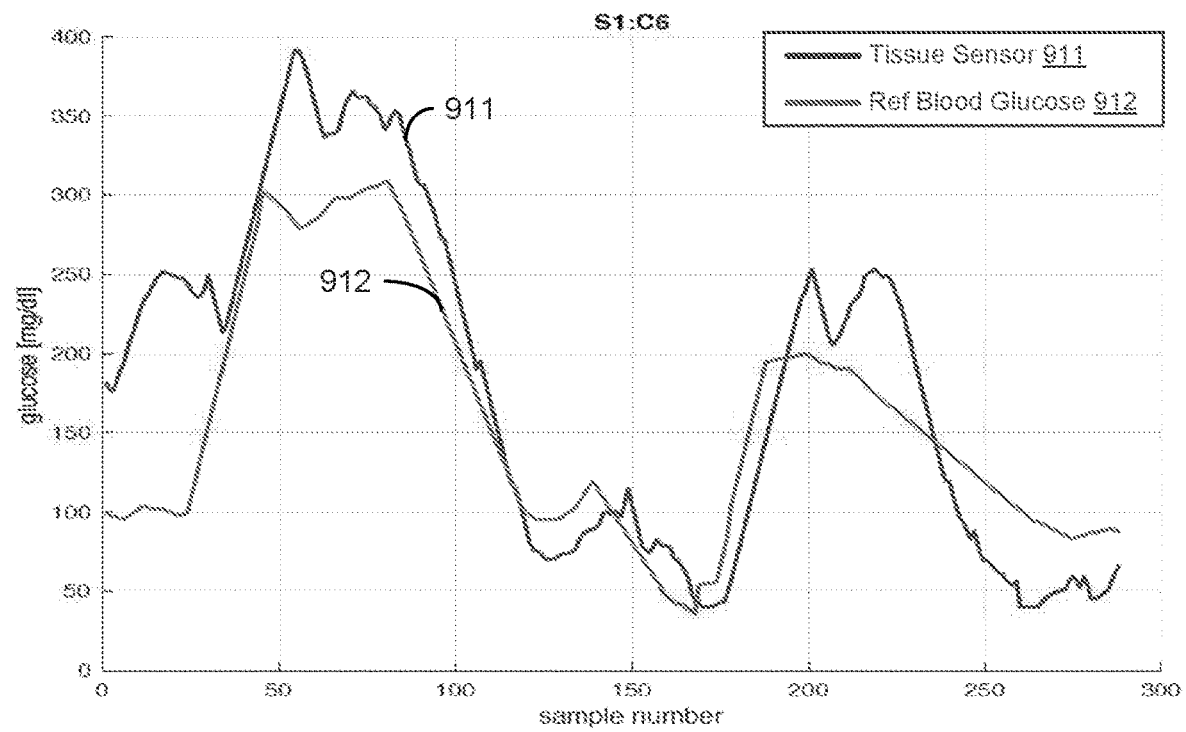
FIGS. 9A-9C show data plots depicting example results from an implementation of an example estimator in continuous mode for a second subject.

The sensor devices were implanted several weeks prior to data collection. On the day of data collection, solutions of glucose and insulin were intravenously injected to create blood glucose excursions typically seen in people with diabetes. Tissue glucose tissue sensor values and tissue oxygen sensor values were collected every two minutes and connected by linear interpolation. Reference blood glucose samples were obtained by phlebotomy and assayed by a standard assay method every 10 to 15 minutes and are connected by linear interpolation and matched to sensor values at 2-minute intervals. The vertical axis of FIGS. 8A and 9A represents concentration, and the horizontal axis represents the series sample number, or time, where each sample is collected at a 2-minute interval. The initiation of data collection is arbitrary, and series data values in FIGS. 8A-8C and FIGS. 9A-9C are respectively aligned in register.

FIG. 8A shows the values obtained by the tissue glucose sensor and reference blood glucose samples for the subject S1:C1. In FIG. 8A, discrete tissue glucose sensor values 811 and the reference blood glucose values 812 are respectively connected by straight lines. As clearly indicated by the data plot, there are substantial differences between the measured sensor values and reference values. The figure illustrates the significant discrepancies between tissue glucose and reference blood glucose values, which may lead to errors in management of a patient's diabetic condition.

FIG. 8B shows the composite error and components of the composite error after application of the estimator 400. The composite error, or difference between the tissue glucose sensor signal and reference blood glucose, shown by the plot line 821. The effect of oxygen measurement error, or the equivalent of $(i_{g_k} - O_k \hat{x}_{k-1})$, is shown in plot line 823. The effect of glucose diffusion, or the equivalent of $L_k \hat{x}_{k-1}$, is shown in plot line 824. The residual error, or the equivalent of $\hat{x}_k$, is shown in the broken line plot 822. Random error was determined to be insignificant in these examples and is not included.

FIG. 8C shows the residual error that is determined by the estimator 400, which corresponds to the estimated blood glucose value compared to the reference blood glucose and the original tissue glucose sensor signal for patient S1:C1. The tissue glucose sensor values 811 and the reference blood glucose values 812 shown in FIG. 8C are the same as those shown in FIG. 8A. Here, FIG. 8C shows the example result of implementing the estimator 400 on the tissue sensor data and reference blood glucose data of the patient S1:C1 to determine the residual error $\hat{x}$, which is added back to the reference blood glucose, to produce the estimated blood glucose, shown by the broken line plot 833.

FIG. 9A shows the values obtained by the tissue glucose sensor and reference blood glucose samples for the subject S1:C6. In FIG. 9A, discrete tissue glucose sensor values 911 and the reference blood glucose values 912 are respectively connected by straight lines. This data demonstrates substantial differences between the measured sensor values and reference values.

Figure 9B:
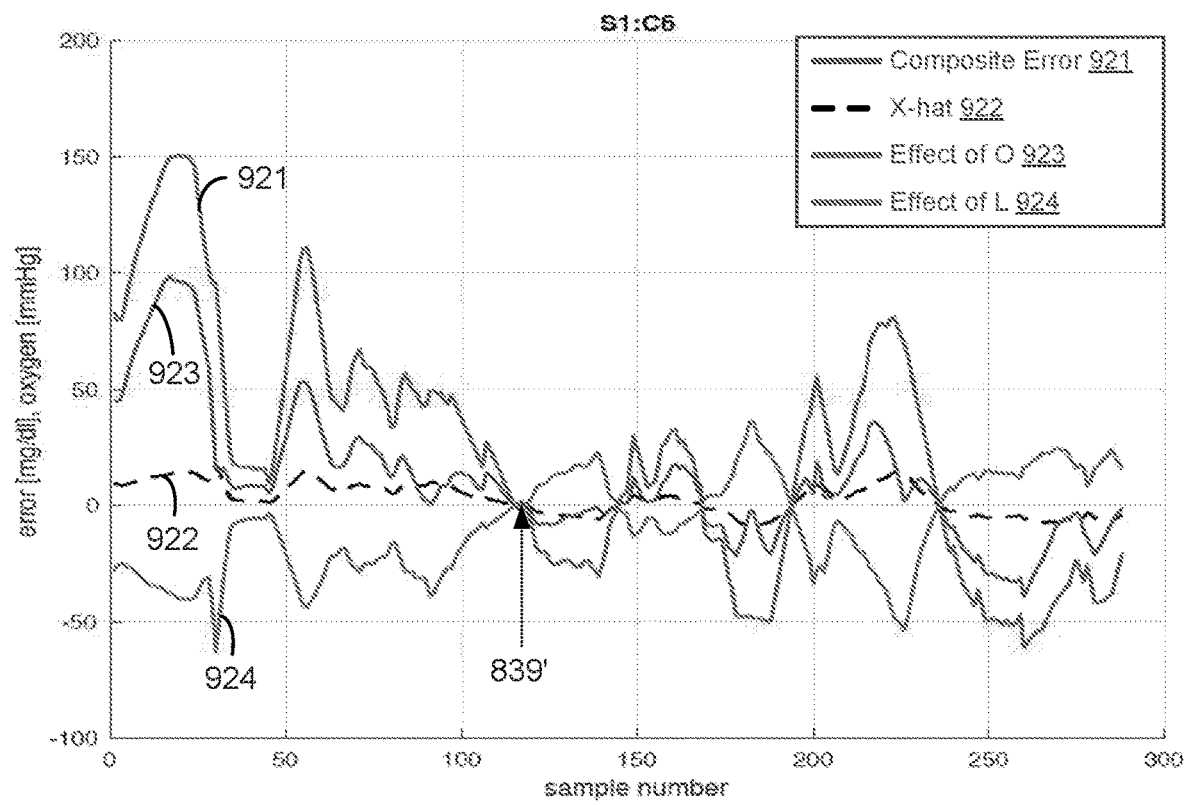

FIG. 9B shows the composite error in plot line 921, the residual error in plot line 922, the effect of measurement error in plot line 923, and the effect of glucose diffusion lag error in plot line 924 that are contained in the tissue sensor signals from FIG. 9A, which are individually displayed after application of the estimator 400, e.g., to segregate the errors.

Figure 9C:
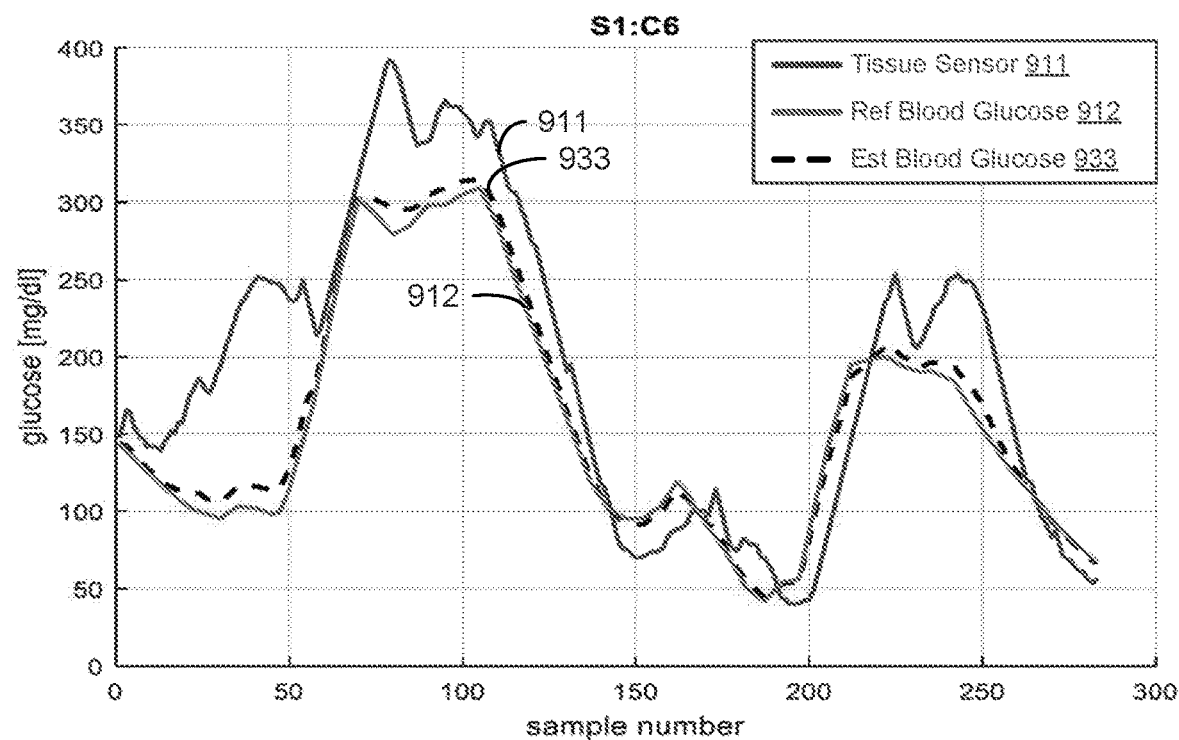

FIG. 9C shows the residual error that is determined by the estimator 400, which corresponds to the estimated blood glucose value, alongside the reference blood glucose and the original tissue glucose sensor signal for patient S1:C6. The tissue glucose sensor values 911 and the reference blood glucose values 912 shown in FIG. 9A are the same as those shown in FIG. 9A. Here, FIG. 9C shows the example result of implementing the estimator 400 on the tissue sensor data and reference blood glucose data of the patient S1:C6 to determine the residual error $\hat{x}$, which is added back to the reference blood glucose, to produce the estimated blood glucose, shown by the broken line plot 933.

Table 2 shows examples of the systematically-varied estimator parameter values used in the example implementations associated with FIGS. 8A-8C, including gain B, Laplace domain glucose lag models (designated in Table 2 as F), oxygen measurement error gains and offsets O, and the resulting MARD values. Table 2 lists these parameter values used in the estimator and their respective results for subject S1:C1. These example results show that appropriate choice of parameter values can have a substantial effect on the estimation.

TABLE 2

| B | F | O (mmHg) | MARD (%)* |
|---|---|---|---|
| 1 | 0 | 5.735 | 2.664 |
|  |  | (constant, std. dev.) |  |
|  |  | 1.0 (constant) | 8.972 |
|  |  | (O × 0.1) − 3.298 | 12.51 |
|  |  | (O × 0.5) − 16.49 | 6.468 |
|  |  | (O × 1.0) − 32.98 | 4.255 ^^ |
|  |  | (O × 2.0) − 65.96 | 2.610 |
|  |  | (O × 5.0) − 164.9 | 0.922 |
| 0.1 | −4/(s + 1) | (O × 1.0) − 32.98 | 0.349 |
| 0.8 |  |  | 1.928 |
| 1.0 |  |  | 2.217 ^^ |
| 2.0 |  |  | 3.219 |
| 10 |  |  | 5.550 |
| 1 | −4/(s + 1) | 0 | 3.685 ^^ |
|  | 4/(s + 1) |  | 474.6 |
|  | −1/(s + 1) |  | 10.19 |
|  | −10/(s + 1) |  | 1.632 |
|  | −4/(0.1 s + 1) |  | 3.589 |
|  | −4/(10 s + 1) |  | 12.30 |
|  | −4/(s + 0.1) |  | 0.728 |
|  | −4/(s + 10) |  | 12.82 |

(^^data used in MARD calculations associated with Table 3)
(*x̄ vs. IRBG, interpolated reference blood glucose)

Table 3 shows example results of MARD calculations from the example implementations of the estimator 400 for the two subjects S1:C1 and S1:C6. Table 3 shows the original MARD values prior to application of the estimator (as shown in the second column of Table 3 labeled "MARD, % Sensor glucose vs. IRBG"); the MARD values obtained using the parameter values identified by "^^", given in Table 2 (as shown in the third column of Table 3 labeled "MARD, % x̄ vs. IRBG), and their differences or improvements (shown in the right-most column of Table 3). Substantial improvement results from use of the estimator 400, e.g., using the parameter values identified by "^^", given in Table 2.

TABLE 3

| Data set | MARD, % Sensor glucose vs. IRBG* | MARD, % x̄ vs. IRBG | Difference (improvement) |
|---|---|---|---|
| S1:C1 | 17.94 | 2.217 | 15.73 |
| S1:C6 | 34.18 | 4.449 | 29.72 |

*IRBG is interpolated reference blood glucose

In all cases for these example implementations, for example, there was only a limited attempt to further refine parameter values that would lead to exquisite matching of the blood glucose estimator and the reference blood glucose, as this would lead to arbitrarily close overlap between the estimated blood glucose and the reference blood glucose, making visualization of the effect less obvious. This was deemed unnecessary for the present demonstration, as the resulting MARD values showed substantial and sufficient improvement. Nevertheless, further adjustment of estimator parameters can lead to a further reduction in MARD.

Figure 11:
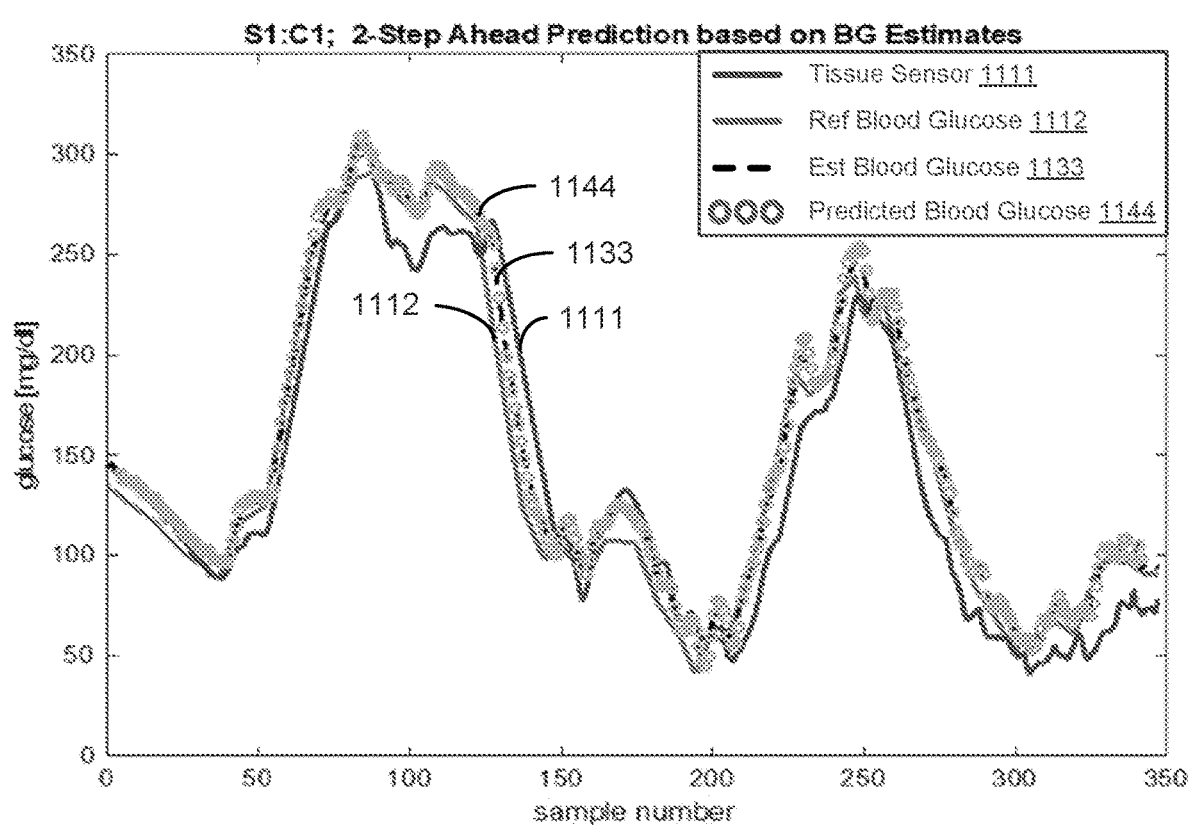
FIG. 11 shows a data plot depicting example results of blood glucose prediction ahead of present time using an example embodiment of the estimator in accordance with the present technology.

Example implementations of discrete-time blood glucose estimation. Blood glucose estimation can also be made in discrete-time, as an alternative to determination of the optimal serial (continuous) blood glucose estimate based on batch methods (like that in FIGS. 8A-8C and 9A-9C). Estimations in discrete-time can be implemented when time-series sensor signals are available at intervals. Although real-time estimation is also a major improvement over correlation, the value may not be expected to exactly match optimal estimator using the same parameter values. FIG. 11 shows data from an example implementation of discrete-time estimations of blood glucose, in addition to predicted blood glucose, discussed later below.

Example implementations of simulated real-time blood glucose estimation.

Figure 10:
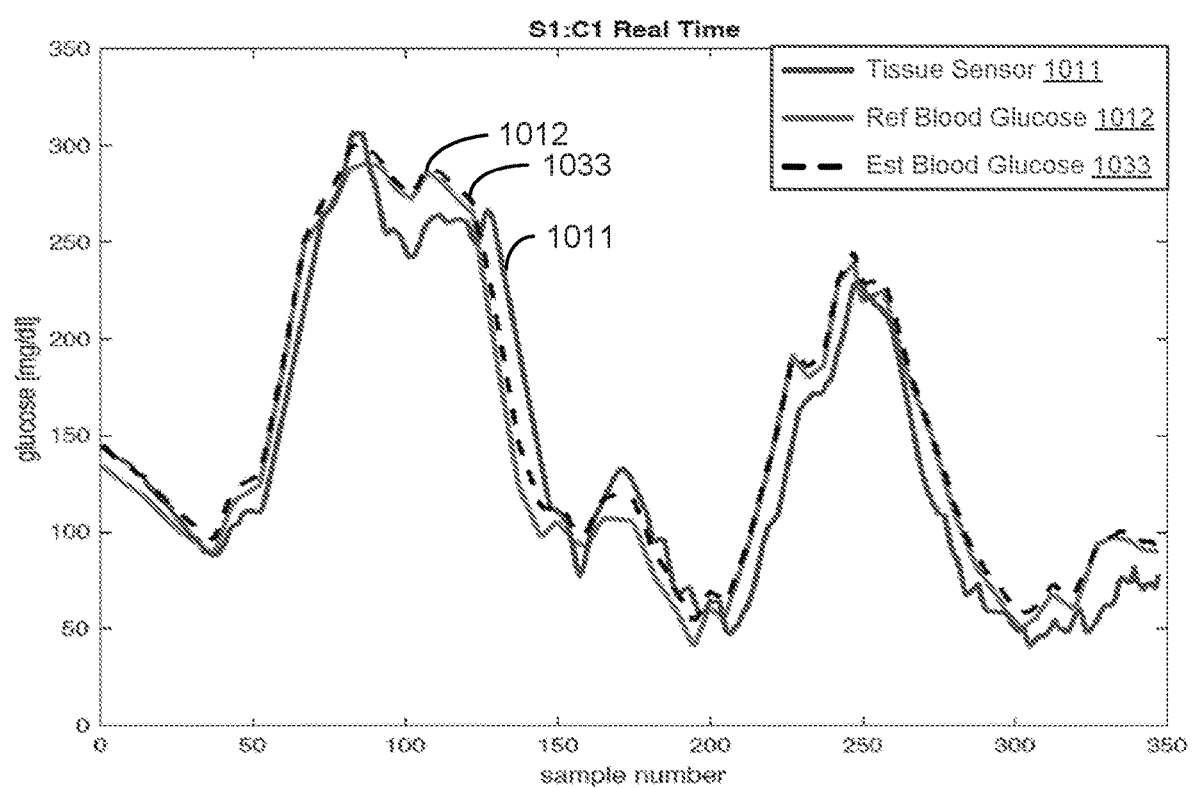
FIG. 10 shows a data plot depicting example results of an application of an example estimator in real-time mode.

FIG. 10 shows a data plot depicting example results of an application of the example estimator 400 in simulated real-time mode. After estimating the measurement and glucose diffusion lag errors, the estimator was directly applied to data as generated in real-time, which can only be simulated in this case. The example simulated real-time application of the estimator was implemented in accordance with the method 750 shown in FIG. 7C, and as described below. These implementations include glucose data obtained from the subject S1:C1.

As shown in FIG. 10, discrete tissue glucose sensor values 1011 and the reference blood glucose values 1012 are plotted to respectively correspond by straight lines. As clearly indicated by the FIG. 10, there are substantial differences between the measured sensor values and reference values. Yet, the estimated blood glucose, shown by the broken line plot 1033, produced by implementing the estimator 400 on the tissue sensor data and reference blood glucose data of the patient S1:C1 shows the close matching of the estimated data to the true blood glucose measured by the patient.

Future blood glucose estimates from recent values. In addition to knowledge of real-time blood glucose estimates, projection of blood glucose estimates ahead of real-time would be of great advantage, allowing anticipation of blood glucose excursions and the effects of therapies. Previous studies based on time-series of actual blood glucose values sampled directly without sensors demonstrated that blood glucose values can be predicted 10 or more minutes ahead of real-time with quantifiable accuracy using a standard autoregressive moving average (ARMA) operator on data from diabetic and non-diabetic subjects.

Blood glucose estimates obtained by use of the disclosed estimator devices, systems and methods can also be applied to predict or infer near-term future blood glucose estimates from previous blood glucose estimate values. Moreover, prediction based on recent blood glucose estimates is a more effective alternative to the use of whole body glucose distribution models, that require detailed information about dynamic insulin availability, which is difficult to obtain.

FIG. 11 shows a data plot depicting example results of a two-step ahead prediction of blood glucose estimates using the estimator 400. In the example implementation, blood glucose values were estimated at least two samples ahead (e.g., 4 minutes) of the tissue signal data, e.g., which can correspond to four minutes ahead of real-time, using a linear auto-regressive moving average predictor applied to real-time blood glucose estimate. As shown in FIG. 11, discrete tissue glucose sensor values 1111 and the reference blood glucose values 1112 are plotted to according to the convention used in FIGS. 8A-8C, for example. The estimated blood glucose, shown by the broken line plot 1133, was produced by implementing the estimator 400 on the tissue sensor data 1111 and reference blood glucose data 1111, which shows the close matching of the estimated data to the true blood glucose of the patient. The two-step ahead predicted values are shown in purple circle line 1144 in FIG. 11. As indicated in the data plot of FIG. 11, the predicted blood glucose line 1144 closely aligns with the estimated blood glucose line 1133. Table 4 summarizes the resulting MARD values associated with this implementation two-step ahead (e.g., 4 minutes) and four-step ahead (e.g., 8 minutes) using this implementation.

Table 4 shows examples of MARD values from tissue glucose prediction ahead of present time using an embodiment of the estimator. Although MARD values increase and estimator accuracy decreases with increased distance ahead of present time, prediction may nevertheless be of significant advantage in certain situations for improved management of blood glucose.

TABLE 4

| Method, vs. IRBG* | MARD (%) |
|---|---|
| Correlation: sensor signal | 17.94 |
| Optimal estimate: x̂ | 2.21 |
| Real-time estimate: x̂ | 6.50 |
| 2-step ahead prediction | 8.82 |
| 4-step ahead prediction | 10.13 |

*IRBG is interpolated reference blood glucose

EXAMPLES

The following examples include embodiments and/or implementations of the disclosed systems, devices and methods for estimating blood glucose parameters.

The disclosed systems, devices and methods provide a new capability for estimating blood glucose concentration from signals of glucose sensors that can provide a close match to the patient's true blood glucose and that can provide a prediction of the patient's future blood glucose (e.g., within several measurement samples or 10 minutes) with tolerable inaccuracy for a patient to make a clinical decision and/or modify behavior for glucose control.

For example, the disclosed systems, devices and methods provide an estimator that can process the obtained glucose signals from a glucose sensor (such as a tissue glucose sensor) with blood glucose reference values and determine an estimation of the composite error between the signals of glucose sensor and the reference blood glucose values, in which the composite error contains measurement error due to variations in tissue oxygen and microcirculatory perfusion, glucose diffusion lag error, random error (e.g., when significant), and residual error. The estimator can also produce an estimated blood glucose based on the difference of the tissue glucose signal and the determined composite error.

In some example implementations of the estimator, the composite error is first determined by subtracting the blood glucose reference from the original tissue glucose signal, then the residual error is estimated from the composite error by subtracting the measurement error, the process error, and random errors, in which residual error is then added back to the reference blood glucose and compared to the original reference blood glucose to estimate accuracy.

In some example implementations, the composite error can be determined by analysis of the component errors (e.g., measurement error, glucose diffusion lag error, random error (e.g., when significant), and residual error), which are individually estimated and subtracted by the estimator from the original tissue sensor signal, leaving an estimate of the reference blood glucose plus the residual error. In some implementations, the measurement error is estimated and subtracted; the glucose diffusional lag error is estimated and subtracted; the random error is identified and subtracted (e.g., if significant); in which, the residual error remains.

In some examples of the estimator, estimation of measurement error uses signals from an implanted tissue oxygen reference sensor operating in parallel with the glucose sensor.

In some examples of the estimator, estimation of measurement error is based on statistical averages of signals from an implanted tissue oxygen reference sensor operating non-simultaneously with the glucose sensor in the same or different individual.

In some examples of the estimator, estimation of the glucose diffusion lag error can be based on a specified portion (e.g., segment) of tissue glucose sensor signal that equals the reference blood glucose and has approximately constant measurement error.

In some examples of the estimator, the blood glucose reference is first subtracted from the composite error, then the measurement error, glucose diffusion lag error, and random error are subtracted, leaving the residual error.

In some examples of the estimator, the measurement error, glucose diffusion lag error, and random error are subtracted directly from the tissue glucose sensor signal, leaving the sum of the residual error and the reference blood glucose.

In some examples of the estimator, the error of tissue glucose sensor signals is compared to reference blood glucose values as mean absolute relative difference, or MARD, which is the mean of the absolute value of the tissue glucose sensor signals processed minus reference blood glucose values divided by the reference blood glucose values.

In such examples where the blood glucose reference is first subtracted from the composite error, then the measurement error, glucose diffusion lag error, and random error are subtracted, leaving the residual error, calculation of MARD can include comparing the residual error plus glucose reference values to glucose reference values.

In such examples where the measurement error, glucose diffusion lag error, and random error are subtracted directly from the tissue glucose sensor signal, leaving the sum of the residual error and the reference blood glucose, calculation of MARD can include adding residual error to glucose reference values to produce an estimate of the reference values and comparison to unprocessed glucose reference values.

In some examples implementations, the estimator implements a method for estimating the error of the tissue glucose sensor signal when there is a temporal sampling mismatch between the reported tissue sensor value and the reference value.

In some examples implementations, the estimator implements a method for predicting tissue sensor glucose concentration into the future when there is minimal temporal sampling error between the reported tissue sensor value and the reference value.

One example embodiment includes a method for estimation of continuous and discrete blood glucose concentration using static and dynamic signals from electrochemical enzyme-based glucose sensors implanted in bodily tissues, in which errors in the signals are specified independently and subtracted to produce an estimate of blood glucose concentration. The errors in the sensor signals can include: measurement error due to oxygen concentration variations in local bodily tissue recorded simultaneously or independently, or not recorded; process errors due to glucose diffusion lags in tissues and diffusion-reaction lags within the sensor itself; and random error—for example—in which said errors in said signals can be reconstructed; in which oxygen measurements are simultaneous; in which oxygen measurements are in time-series; in which said method and means operates in the anticausal mode, where signals from sensors implanted in tissues are used to estimate blood glucose concentration; in which various continuous and discrete implementations and variations of said method are included; and/or in which use of said method allows accurate estimation of blood glucose concentration.

In some examples of the method, the sensor is inserted subcutaneously.

In some examples of the method, the sensor is deployed cutaneously.

In some examples, the method includes identifying values of parameters, including variations.

In some examples, the method includes using series estimated blood values to predict future blood glucose values using autoregressive moving average (ARMA) system.

In some examples, the method includes applying the estimated blood glucose to operate over the entire range of diabetic blood glucose excursions.

In some examples, the method includes estimating error in diabetic and non-diabetic blood glucose excursion due to the interval of telemetry signal transmission.

In some embodiments in accordance with the present technology (example A1), a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values, wherein when no temporal match is determined, creating a matched blood glucose model to provide the matched blood glucose reference values; isolating error associated with the matched blood glucose reference values to determine a residual error time series, wherein the isolated error includes a composite error; and producing estimated blood glucose values for true blood glucose of the subject by adding the reference blood glucose concentration values to the residual error time series.

Example A2 includes the method of example A1, further comprising providing the estimated blood glucose values to a controller associated with an insulin delivery device to affect an insulin delivery control to the insulin delivery device.

Example A3 includes the method of example A1, further comprising providing the estimated blood glucose values to a controller associated with the glucose sensor to affect a glucose measurement parameter of the glucose sensor.

Example A4 includes the method of example A1, wherein the isolating the error includes determining the one or more of the composite error, the process error, and the random error individually by subtracting the reference blood glucose concentration values from the matched blood glucose reference values to determine the composite error, subtracting measurement error from the determined composite error to determine process and random error, and subtracting the random error from the determined process and random error to determine the residual error time series.

Example A5 includes the method of example A1, wherein the glucose sensor includes one or both of an enzyme-based and a complexation-based glucose sensor.

Example A6 includes the method of example A1, wherein the glucose sensor includes a wearable glucose sensor implanted subcutaneously in tissue of the subject, inserted percutaneously through the skin in tissue of the subject, or deployed cutaneously on surface of the skin of the subject.

In some embodiments in accordance with the present technology (example A7), a device for estimating blood glucose concentration from signals of glucose sensors includes a data processing device comprising a processor and a memory in communication with a glucose sensor, the data processing unit including an estimator module operable to: obtain a set of time-series values that includes tissue glucose sensor values from a glucose sensor and reference blood glucose concentration values associated with a subject, generate a set of matched blood glucose reference values by determining a temporal matching of the tissue glucose sensor values and the reference blood glucose concentration values, wherein when no temporal match is determined, creating a matched blood glucose model to provide the matched blood glucose reference values, isolate error associated with the matched blood glucose reference values to determine a residual error time series, wherein the isolated error includes a composite error, and produce estimated blood glucose values for true blood glucose of the subject by adding the reference blood glucose concentration values to the residual error time series.

Example A8 includes the device of example A7, wherein the estimator module is operable to provide the estimated blood glucose values to a controller associated with an insulin delivery device, in communication with the data processing device, to affect an insulin delivery control to the insulin delivery device.

Example A9 includes the device of example A7, wherein the estimator module is operable to provide the estimated blood glucose values to a controller associated with the glucose sensor to affect a glucose measurement parameter of the glucose sensor.

Example A10 includes the device of example A7, wherein the estimator module is operable to isolate error by determining the one or more of the composite error, the process error, and the random error individually by subtracting the reference blood glucose concentration values from the matched blood glucose reference values to determine the composite error, subtracting measurement error from the determined composite error to determine process and random error, and subtracting the random error from the determined process and random error to determine the residual error time series.

Example A11 includes the device of example A7, wherein the glucose sensor includes one or both of an enzyme-based and a complexation-based glucose sensor.

Example A12 includes the device of example A7, wherein the glucose sensor includes a wearable glucose sensor implanted subcutaneously in tissue of the subject, inserted percutaneously through the skin in tissue of the subject, or deployed cutaneously on surface of the skin of the subject.

In some embodiments in accordance with the present technology (example A13), a system for estimating blood glucose concentration from signals of glucose sensors includes a glucose sensor acquire glucose measurements from a subject; and a data processing device comprising a processor and a memory in communication with the glucose sensor, the data processing unit including an estimator module operable to: obtain a set of time-series values that includes tissue glucose sensor values from a glucose sensor and reference blood glucose concentration values associated with a subject, generate a set of matched blood glucose reference values by determining a temporal matching of the tissue glucose sensor values and the reference blood glucose concentration values, wherein when no temporal match is determined, creating a matched blood glucose model to provide the matched blood glucose reference values, isolate error associated with the matched blood glucose reference values to determine a residual error time series, wherein the isolated error includes a composite error, and produce estimated blood glucose values for true blood glucose of the subject by adding the reference blood glucose concentration values to the residual error time series.

Example A14 includes the system of example A13, further includes an insulin delivery device, in communication with the data processing device, to operable to administer a dose of insulin to the subject based on an insulin delivery control provided by a controller of the insulin delivery device, wherein the estimator module is operable to provide the estimated blood glucose values to the controller to affect the insulin delivery control to a dose administration by the insulin delivery device.

Example A15 includes the system of example A13, wherein the estimator module is operable to provide the estimated blood glucose values to a controller associated with the glucose sensor to affect a glucose measurement parameter of the glucose sensor.

Example A16 includes the system of example A13, wherein the estimator module is operable to isolate error by determining the one or more of the composite error, the process error, and the random error individually by subtracting the reference blood glucose concentration values from the matched blood glucose reference values to determine the composite error, subtracting measurement error from the determined composite error to determine process and random error, and subtracting the random error from the determined process and random error to determine the residual error time series.

Example A17 includes the system of example A13, wherein the glucose sensor includes one or both of an enzyme-based and a complexation-based glucose sensor.

Example A18 includes the system of example A13, wherein the glucose sensor includes a wearable glucose sensor implanted subcutaneously in tissue of the subject, inserted percutaneously through the skin in tissue of the subject, or deployed cutaneously on surface of the skin of the subject.

In some embodiments in accordance with the present technology (example B1), a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; isolating error associated with the matched blood glucose reference values to determine a residual error time series, wherein the isolated error includes a composite error comprising a measurement error, a process error, and random error; and producing estimated blood glucose values for true blood glucose of the subject by adding the reference blood glucose concentration values to the residual error time series.

Example B2 includes the method of any of examples B1-B8, further comprising providing the estimated blood glucose values to a controller associated with an insulin delivery device to affect an insulin delivery control to the insulin delivery device.

Example B3 includes the method of any of examples B1-B8, further comprising providing the estimated blood glucose values to a controller associated with the glucose sensor to affect a glucose measurement parameter of the glucose sensor.

Example B4 includes the method of any of examples B1-B8, wherein the isolating the error includes determining the composite error by subtracting the reference blood glucose concentration values from the matched blood glucose reference values; estimating the measurement error, the process error, and random error; and subtracting the measurement error, the process error, and the random error from the determined composite error to determine the residual error time series.

Example B5 includes the method of any of examples B1-B8, wherein, when no temporal match is determined, the method comprises creating a matched blood glucose model to provide the matched blood glucose reference values.

Example B6 includes the method of any of examples B1-B8, wherein the glucose sensor includes one or both of an enzyme-based and a complexation-based glucose sensor.

Example B7 includes the method of any of examples B1-B8, wherein the glucose sensor includes a wearable glucose sensor that is implanted subcutaneously in tissue of the subject, inserted percutaneously through the skin in tissue of the subject, or deployed cutaneously on surface of the skin of the subject.

Example B8 includes the method of any of examples B1-B8, further comprising using the estimated blood glucose values, predicting a future blood glucose value at least one sample ahead of the obtained tissue glucose sensor values.

In some embodiments in accordance with the present technology (example B9), a device for estimating blood glucose concentration from signals of glucose sensors includes a data processing device comprising a processor and a memory in communication with a glucose sensor, the data processing unit including an estimator module operable to: obtain a set of time-series values that includes tissue glucose sensor values from a glucose sensor and reference blood glucose concentration values associated with a subject, generate a set of matched blood glucose reference values by determining a temporal matching of the tissue glucose sensor values and the reference blood glucose concentration values, isolate error associated with the matched blood glucose reference values to determine a residual error time series, wherein the isolated error includes a composite error comprising a measurement error, a process error, and random error, and produce estimated blood glucose values for true blood glucose of the subject by adding the reference blood glucose concentration values to the residual error time series.

Example B10 includes the device of any of examples B9-B14, wherein the estimator module is operable to provide the estimated blood glucose values to a controller associated with an insulin delivery device, in communication with the data processing device, to affect an insulin delivery control to the insulin delivery device.

Example B11 includes the device of any of examples B9-B14, wherein the estimator module is operable to provide the estimated blood glucose values to a controller associated with the glucose sensor to affect a glucose measurement parameter of the glucose sensor.

Example B12 includes the device of any of examples B9-B14, wherein the estimator module is operable to the isolate the error by determining the composite error, which includes subtracting the reference blood glucose concentration values from the matched blood glucose reference values; estimating the measurement error, the process error, and random error; and subtracting the measurement error, the process error, and the random error from the determined composite error to determine the residual error time series.

Example B13 includes the device of any of examples B9-B14, wherein the glucose sensor includes one or both of an enzyme-based and a complexation-based glucose sensor.

Example B14 includes the device of any of examples B9-B14, wherein the glucose sensor includes a wearable glucose sensor that is implanted subcutaneously in tissue of the subject, inserted percutaneously through the skin in tissue of the subject, or deployed cutaneously on surface of the skin of the subject.

In some embodiments in accordance with the present technology (example B15), a system for estimating blood glucose concentration from signals of glucose sensors includes a glucose sensor acquire glucose measurements from a subject; and a data processing device comprising a processor and a memory in communication with the glucose sensor, the data processing unit including an estimator module operable to: obtain a set of time-series values that includes tissue glucose sensor values from a glucose sensor and reference blood glucose concentration values associated with a subject, generate a set of matched blood glucose reference values by determining a temporal matching of the tissue glucose sensor values and the reference blood glucose concentration values, isolate error associated with the matched blood glucose reference values to determine a residual error time series, wherein the isolated error includes a composite error comprising a measurement error, a process error, and random error, and produce estimated blood glucose values for true blood glucose of the subject by adding the reference blood glucose concentration values to the residual error time series.

Example B16 includes the system of any of examples B15-B20, further comprising an insulin delivery device, in communication with the data processing device, to operable to administer a dose of insulin to the subject based on an insulin delivery control provided by a controller of the insulin delivery device, wherein the estimator module is operable to provide the estimated blood glucose values to the controller to affect the insulin delivery control to a dose administration by the insulin delivery device.

Example B17 includes the system of any of examples B15-B20, wherein the estimator module is operable to provide the estimated blood glucose values to a controller associated with the glucose sensor to affect a glucose measurement parameter of the glucose sensor.

Example B18 includes the system of any of examples B15-B20, wherein the estimator module is operable to the isolate the error by determining the composite error, which includes subtracting the reference blood glucose concentration values from the matched blood glucose reference values; estimating the measurement error, the process error, and random error; and subtracting the measurement error, the process error, and the random error from the determined composite error to determine the residual error time series.

Example B19 includes the system of any of examples B15-B20, wherein the glucose sensor includes one or both of an enzyme-based and a complexation-based glucose sensor.

Example B20 includes the system of any of examples B15-B20, wherein the glucose sensor includes a wearable glucose sensor that is implanted subcutaneously in tissue of the subject, inserted percutaneously through the skin in tissue of the subject, or deployed cutaneously on surface of the skin of the subject.

In some embodiments in accordance with the present technology (example B21), a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; determining a composite error in measured glucose by subtracting the reference blood glucose concentration values from the matched blood glucose reference values; determining a residual error of the set of time-series values by estimating and subtracting at least some of individual components of the determined composite error, wherein the components of the composite error include measurement error, process error, and random error; and producing estimated blood glucose values for true blood glucose of the subject by adding the reference blood glucose concentration values to the determined residual error.

Example B22 includes the method of any of examples B21-B30, further comprising determining a mean absolute relative difference (MARD) between the estimated blood glucose values and the reference blood glucose concentration values, wherein the MARD is the mean of the absolute value of the estimated blood glucose values minus the reference blood glucose values divided by the reference blood glucose concentration values.

Example B23 includes the method of any of examples B21-B30, further comprising using the estimated blood glucose values, predicting a future blood glucose value at least one sample ahead of the obtained tissue glucose sensor values.

Example B24 includes the method of any of examples B21-B30, further comprising providing the estimated blood glucose values to a controller associated with an insulin delivery device to affect an insulin delivery control to the insulin delivery device; and/or providing the estimated blood glucose values to a controller associated with the glucose sensor to affect a glucose measurement parameter of the glucose sensor.

Example B25 includes the method of any of examples B21-B30, wherein, when no temporal match is determined, the method comprises creating a matched blood glucose model to produce the matched blood glucose reference values.

Example B26 includes the method of any of examples B21-B30, wherein the glucose sensor includes one or both of an enzyme-based and a complexation-based glucose sensor.

Example B27 includes the method of any of examples B21-B30, wherein the glucose sensor includes a wearable glucose sensor that is implanted subcutaneously in tissue of the subject, inserted percutaneously through the skin in tissue of the subject, or deployed cutaneously on surface of the skin of the subject.

Example B28 includes the method of any of examples B21-B30, wherein the estimating the measurement error includes using signals from an implanted tissue oxygen reference sensor operating in parallel with the glucose sensor.

Example B29 includes the method of any of examples B21-B30, wherein the estimating the measurement error is based on statistical averages of signals obtained from an implanted tissue oxygen reference sensor operating non-simultaneously with the glucose sensor in the subject or a different individual.

Example B30 includes the method of any of examples B21-B30, wherein the estimating the process error includes identifying a portion of the time-series values that includes the tissue glucose sensor values that equals the reference blood glucose and has a substantially constant measurement error.

In some embodiments in accordance with the present technology (example B31), a method for estimating blood glucose concentration from signals of glucose sensors includes obtaining a set of time-series values that includes tissue glucose sensor values from a glucose sensor and reference blood glucose concentration values associated with a subject; generating a set of matched blood glucose reference values by determining a temporal matching of the tissue glucose sensor values and the reference blood glucose concentration values; determining a composite error in measured glucose by subtracting the reference blood glucose concentration values from the matched blood glucose reference values; estimating individual error components in measured glucose including measurement error, process error, and random error; and producing estimated reference blood glucose values of the subject by subtracting the estimated error components from the matched blood glucose reference values.

Example B32 includes the method of any of examples B31-B37, further comprising determining a mean absolute relative difference (MARD) between the estimated reference blood glucose values and the reference blood glucose concentration values, wherein the MARD is the mean of the absolute value of the estimated reference blood glucose values minus the reference blood glucose values divided by the reference blood glucose concentration values.

Example B33 includes the method of any of examples B31-B37, further comprising using the estimated reference blood glucose values, predicting a future blood glucose value at least one sample ahead of the obtained tissue glucose sensor values.

Example B34 includes the method of any of examples B31-B37, further comprising providing the estimated blood glucose values to a controller associated with an insulin delivery device to affect an insulin delivery control to the insulin delivery device; and/or providing the estimated blood glucose values to a controller associated with the glucose sensor to affect a glucose measurement parameter of the glucose sensor.

Example B35 includes the method of any of examples B31-B37, wherein, when no temporal match is determined, the method comprises creating a matched blood glucose model to produce the matched blood glucose reference values.

Example B36 includes the method of any of examples B31-B37, wherein the glucose sensor includes one or both of an enzyme-based and a complexation-based glucose sensor.

Example B37 includes the method of any of examples B31-B37, wherein the glucose sensor includes a wearable glucose sensor that is implanted subcutaneously in tissue of the subject, inserted percutaneously through the skin in tissue of the subject, or deployed cutaneously on surface of the skin of the subject.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A system for estimating blood glucose concentration from signals of glucose sensors, comprising:
    a glucose sensor to acquire glucose measurements from a subject; and
    a data processing device comprising a processor and a memory in communication with the glucose sensor, the data processing device including an estimator module operable to:
        obtain a set of time-series values that includes tissue glucose sensor values from a glucose sensor and reference blood glucose concentration values associated with a subject,
        generate a set of matched blood glucose reference values by determining a temporal matching of the tissue glucose sensor values and the reference blood glucose concentration values,
        isolate error from a composite error associated with the matched blood glucose reference values to determine a residual error time series, wherein the composite error comprises a measurement error, a process error, random error, and residual error, wherein the estimator module is operable to isolate the error by (a) determining the composite error, which includes subtracting the reference blood glucose concentration values from the matched blood glucose reference values, (b) estimating the measurement error, the process error, and random error, and (c) individually subtracting the measurement error, the process error, and the random error from the determined composite error to determine the residual error time series, and
        produce estimated blood glucose values for true blood glucose of the subject by adding the reference blood glucose concentration values to the residual error time series.

2. The system of claim 1, further comprising:
    an insulin delivery device, in communication with the data processing device, to operable to administer a dose of insulin to the subject based on an insulin delivery control provided by a controller of the insulin delivery device,
    wherein the estimator module is operable to provide the estimated blood glucose values to the controller to affect the insulin delivery control to a dose administration by the insulin delivery device.

3. The system of claim 1, wherein the estimator module is operable to provide the estimated blood glucose values to a controller associated with the glucose sensor to affect a glucose measurement parameter of the glucose sensor.

4. The system of claim 1, wherein the glucose sensor includes one or both of an enzyme-based and a complexation-based glucose sensor.

5. The system of claim 1, wherein the glucose sensor includes a wearable glucose sensor that is implanted subcutaneously in tissue of the subject, inserted percutaneously through skin in tissue of the subject, or deployed cutaneously on surface of the skin of the subject.

6. The method of claim 1, wherein the estimator module is operable to determine the composite error, instead of by the subtracting, by (i) identifying whether a segment of the set of time-series values rises at a maximal sustained rate at least equal to a rise of the reference blood glucose concentration values while the measurement error and process error are substantially constant, and, if the segment is identified, then by (ii) determining the measurement error, the process error, and the residual error as substantially zero and (iii) assigning the composite error as equal to the reference blood glucose concentration values.

7. A method for estimating blood glucose concentration from signals of glucose sensors, comprising:
    obtaining a set of time-series values that includes tissue glucose sensor values from a glucose sensor and reference blood glucose concentration values associated with a subject;
    generating a set of matched blood glucose reference values by determining a temporal matching of the tissue glucose sensor values and the reference blood glucose concentration values;
    determining a composite error in measured glucose by subtracting the reference blood glucose concentration values from the matched blood glucose reference values, wherein the composite error comprises a measurement error, a process error, random error, and residual error;
    determining the residual error of the set of time-series values by estimating and subtracting at least some of individual components of the determined composite error; and producing estimated blood glucose values for true blood glucose of the subject by adding the reference blood glucose concentration values to the determined residual error.

8. The method of claim 7, further comprising:
determining a mean absolute relative difference (MARD) between the estimated blood glucose values and the reference blood glucose concentration values, wherein the MARD is the mean of the absolute value of the estimated blood glucose values minus the reference blood glucose values divided by the reference blood glucose concentration values.

9. The method of claim 7, further comprising:
using the estimated blood glucose values, predicting a future blood glucose value at least one sample ahead of the obtained tissue glucose sensor values.

10. The method of claim 7, further comprising:
providing the estimated blood glucose values to a controller associated with an insulin delivery device to affect an insulin delivery control to the insulin delivery device; and/or
providing the estimated blood glucose values to a controller associated with the glucose sensor to affect a glucose measurement parameter of the glucose sensor.

11. The method of claim 7, wherein, when no temporal match is determined, the method comprises creating a matched blood glucose model to produce the matched blood glucose reference values.

12. The method of claim 7, wherein the glucose sensor includes one or both of an enzyme-based and a complexation-based glucose sensor.

13. The method of claim 7, wherein the glucose sensor includes a wearable glucose sensor that is implanted subcutaneously in tissue of the subject, inserted percutaneously through skin in tissue of the subject, or deployed cutaneously on surface of the skin of the subject.

14. The method of claim 7, wherein the estimating the measurement error includes using signals from an implanted tissue oxygen reference sensor operating in parallel with the glucose sensor.

15. The method of claim 7, wherein the estimating the measurement error is based on statistical averages of signals obtained from an implanted tissue oxygen reference sensor operating non-simultaneously with the glucose sensor in the subject or a different individual.

16. The method of claim 7, wherein the estimating the process error includes identifying a portion of the time-series values that includes the tissue glucose sensor values that equals the reference blood glucose and has a substantially constant measurement error.

17. A method for estimating blood glucose concentration from signals of glucose sensors, comprising:
obtaining a set of time-series values that includes tissue glucose sensor values from a glucose sensor and reference blood glucose concentration values associated with a subject;
generating a set of matched blood glucose reference values by determining a temporal matching of the tissue glucose sensor values and the reference blood glucose concentration values;
determining a composite error in measured glucose by subtracting the reference blood glucose concentration values from the matched blood glucose reference values, wherein the composite error comprises a measurement error, a process error, and random error;
estimating individual error components in measured glucose including the measurement error, the process error, and the random error; and
producing estimated reference blood glucose values of the subject by subtracting the estimated individual error components from the matched blood glucose reference values.

18. The method of claim 17, further comprising:
determining a mean absolute relative difference (MARD) between the estimated reference blood glucose values and the reference blood glucose concentration values, wherein the MARD is the mean of the absolute value of the estimated reference blood glucose values minus the reference blood glucose values divided by the reference blood glucose concentration values.

19. The method of claim 17, further comprising:
using the estimated reference blood glucose values, predicting a future blood glucose value at least one sample ahead of the obtained tissue glucose sensor values.

20. The method of claim 17, further comprising:
providing the estimated blood glucose values to a controller associated with an insulin delivery device to affect an insulin delivery control to the insulin delivery device; and/or
providing the estimated blood glucose values to a controller associated with the glucose sensor to affect a glucose measurement parameter of the glucose sensor.

21. The method of claim 17, wherein, when no temporal match is determined, the method comprises creating a matched blood glucose model to produce the matched blood glucose reference values.

22. The method of claim 17, wherein the glucose sensor includes one or both of an enzyme-based and a complexation-based glucose sensor.

23. The method of claim 17, wherein the glucose sensor includes a wearable glucose sensor that is implanted subcutaneously in tissue of the subject, inserted percutaneously through skin in tissue of the subject, or deployed cutaneously on surface of the skin of the subject.

* * * * *